(12) United States Patent
Sowemimo-Coker et al.

(10) Patent No.: US 6,235,508 B1
(45) Date of Patent: *May 22, 2001

(54) METHOD OF INACTIVATION OF VIRAL AND BACTERIAL BLOOD CONTAMINANTS

(75) Inventors: Samuel O. Sowemimo-Coker, Arcadia; Nagender Yerram, So. Pasadena; Raymond P. Goodrich, Jr., Pasadena, all of CA (US); Matthew S. Platz, Columbus, OH (US)

(73) Assignee: Baxter International Inc., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/153,657

(22) Filed: Sep. 15, 1998

Related U.S. Application Data

(63) Continuation of application No. 08/480,271, filed on Jun. 7, 1995, now Pat. No. 5,955,256.

(51) Int. Cl.$^7$ .................................................. C12N 13/00
(52) U.S. Cl. ........................................ 435/173.1; 435/173.3
(58) Field of Search ............................ 435/2, 173.1, 173.3

(56) References Cited

U.S. PATENT DOCUMENTS

| | | | |
|---|---|---|---|
| 4,590,275 | 5/1986 | Cox et al. | 546/62 |
| 4,613,322 | 9/1986 | Edelson | 604/6 |
| 4,742,066 | 5/1988 | Deckner et al. | 514/311 |
| 4,748,120 | 5/1988 | Wiesehahn | 435/173.1 |
| 4,878,891 | 11/1989 | Judy et al. | 604/5 |
| 4,889,129 | 12/1989 | Dougherty et al. | 128/664 |
| 4,927,762 | 5/1990 | Darfler | 435/240.31 |
| 5,120,649 | 6/1992 | Horowitz et al. | 435/173.1 |
| 5,176,921 | 1/1993 | Wiesehahn et al. | 424/529 |
| 5,216,176 | 6/1993 | Heindel et al. | 549/280 |
| 5,232,844 | 8/1993 | Horowitz et al. | 435/173.1 |
| 5,516,629 | 5/1996 | Park et al. | 435/2 |
| 5,587,490 | 12/1996 | Goodrich, Jr. et al. | 549/282 |
| 5,798,238 | * 8/1998 | Goodrich, Jr. et al. | 435/173.3 |

OTHER PUBLICATIONS

Fujita and Matsuo (1993) Photomedicine and Photobiology 15:45.
Goodrich et al. (1994) Proc. Natl. Acad. Sci. USA 91:5552.
Midden (1988) in *Psoralen DNA Photobiology* vol. II, CRC Press, Chapter 4, pp. 1–49.
Rodighiero et al. (1988) in *Psoralen DNA Photobiology* vol. I, CRC Press, Chapter 2, pp. 37–114.

* cited by examiner

*Primary Examiner*—Jon P. Weber
(74) *Attorney, Agent, or Firm*—Margaret M. Wall; Denise M. Serewicz; Michael C. Mayo

(57) ABSTRACT

Viral and bacterial contaminants present in biological solutions are inactivated by mixing one of a novel class of photosensitizer with said solution and irradiating the mixture. Quinoline and quinolone compounds are useful as photosensitizers in this method. With certain photosensitizers a blocking agent may also be employed.

10 Claims, 14 Drawing Sheets

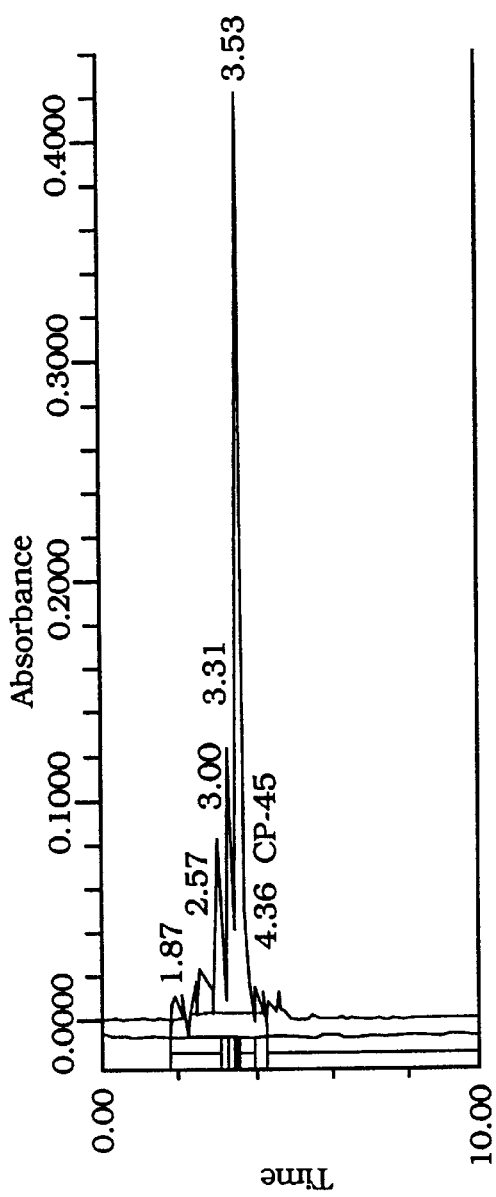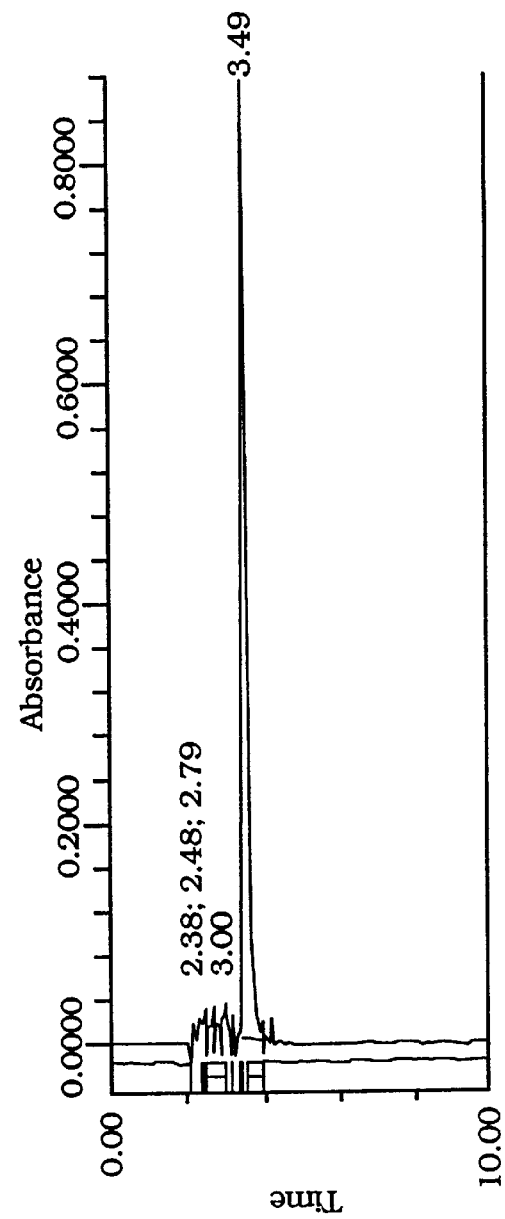
FIG. 8A
FIG. 8B

METHOD OF INACTIVATION OF VIRAL AND BACTERIAL BLOOD CONTAMINANTS

RELATED APPLICATIONS

This application is a continuation of U.S. Ser. No. 08/480,271, filed Jun. 7, 1995, now U.S. Pat. No. 5,955,256, which is incorporated by reference herein in its entirety.

FIELD OF THE INVENTION

This invention relates to the general field of the inactivation of viral and bacterial contamination of blood and blood products including compositions comprising peripheral blood cells (red blood cells, platelets, leukocytes, stem cells, etc.), plasma protein fractions (albumin, clotting factors, etc.) from collected whole blood, the blood of virally infected persons, ex vivo media used in the preparation of antiviral vaccines, and cell culture media such as fetal bovine serum, bovine serum or products derived from these sources.

BACKGROUND OF THE INVENTION

A major concern in the transfusion of donated, stored whole human blood or the various blood cells or protein fractions isolated from whole blood is the possibility of viral contamination. of particular concern are the blood-borne viruses that cause hepatitis (especially hepatitis A, hepatitis B, and hepatitis C) and acquired immune deficiency syndrome (AIDS). While any number of cell washing protocols may reduce the viral contamination load for samples of blood cells, by physical elution of the much smaller virus particles, such washing alone is insufficient to reduce viral contamination to safe levels. In fact, some viruses are believed to be cell-associated, and unlikely to be removed by extensive washing and centrifugal pelleting of the cells. Current theory suggests that safe levels will ultimately require at least a 6 log (6 orders of magnitude) demonstrated reduction in infectious viral titer for cellular blood components. This 6 log threshold may be greater for plasma protein components, especially the clotting factors (Factor VIII, Factor IX) that are administered throughout the life of some hemophilia patients.

All blood collected in the United States is now screened for six infectious agents: HIV-1, HIV-2, HTLV-1, hepatitis B virus, hepatitis C virus and syphilis. Additionally, donors are screened for risk factors, and potential donors are eliminated that are considered at risk for the HIV virus. Despite these measures, the risk of becoming infected by a potentially deadly virus or bacteria via the transfusion of blood or blood products remains serious. Screens for contaminants are by nature not foolproof. There is also the quite likely occurrence of new infectious agents that enter the blood supply before the significance of the event is known. For example, by the end of June 1992, the Center for Disease Control reports that 4,959 AIDS cases could be traced to the receipt of blood transfusions, blood components or tissue.

Viral inactivation by stringent sterilization is not acceptable since this could also destroy the functional components of the blood, particularly the erythrocytes (red blood cells) and thrombocytes (platelets) and the labile plasma proteins, such as clotting factor VIII. Viable RBC's can be characterized by one or more of the following: capability of synthesizing ATP; cell morphology; $P_{50}$ values; filterability or deformability; oxyhemoglobin, methemoglobin and hemochrome values; MCV, MCH, and MCHC values; cell enzyme activity; and in vivo survival. Thus, if virally inactivated cells are damaged to the extent that the cells are not capable of metabolizing or synthesizing ATP, or the cell circulation is compromised, then their utility in transfusion medicine is compromised.

Viral inactivation by stringent steam sterilization is not acceptable since this also destroys the functional components of the blood, particularly the blood cells and plasma proteins. Dry heat sterilization, like wet steam, is harmful to blood cells and blood proteins at the levels needed to reduce viral infectivity. Use of stabilizing agents such as carbohydrates does not provide sufficient protection to the delicate blood cells and proteins from the general effects of exposure to high temperature and pressure.

Methods that are currently employed with purified plasma protein fractions, often followed by lyophilization of the protein preparation, include treatment with organic solvents and heat or extraction with detergents to disrupt the lipid coat of membrane enveloped viruses. Lyophilization (freeze-drying) alone has not proven sufficient to inactivate viruses, or to render blood proteins sufficiently stable to the effects of heat sterilization. The organic solvent or detergent method employed with purified blood proteins cannot be used with blood cells as these chemicals destroy the lipid membrane that surrounds the cells.

Another viral inactivation approach for plasma proteins first demonstrated in 1958 has involved the use of a chemical compound, beta-propiolactone, with ultraviolet (UV) irradiation. This method has not found acceptance in the United States due to concern over the toxicity of beta-propiolactone in the amounts used to achieve some demonstrable viral inactivation and also due to unacceptable levels of damage to the proteins caused by the chemical agents. Concern has also been raised over the explosive potential for beta-propiolactone as well.

There is significant interest in an effective viral inactivation treatment for human blood components, which will not damage the valuable blood cells or proteins. The treatment must be nontoxic and selective for viruses, while allowing the intermingled blood cells or proteins to survive unharmed.

There is an immediate need to develop protocols for the inactivation of viruses that can be present in the human red blood cell supply. For example, only recently has a test been developed for Non A, Non B hepatitis, but such screening methods, while reducing the incidence of viral transmission, do not make the blood supply completely safe or virus free. Current statistics indicate that the transfusion risk per unit of transfused blood is as high as 1:3,000 for Non A, Non B hepatitis (hepatitis C), and ranges from 1:60,000 to 1:225,000 for HIV, depending on geographic location. Clearly, it is desirable to develop a method which inactivates or removes virus indiscriminately from the blood.

Contamination problems also exist for blood plasma protein fractions, such as plasma fractions containing immune globulins and clotting factors. For example, new cases of non A, non B hepatitis and hepatitis A have occurred in hemophilia patients receiving protein fractions containing Factor VIII which have been treated for viral inactivation according to approved methods. Therefore, there is a need for improved viral inactivation treatment of blood protein fractions.

The ability to inactivate bacterial contaminants from blood and blood products may be as critical as reducing viral contaminants. Between 1986 and 1991, the Food and Drug Administration reported that 15.9% of all transfusion related fatalities were associated with the transfusion of bacterially contaminated blood components. Most of these fatalities were due to the transfusion of bacterially contaminated platelets.

Psoralens are naturally occurring compounds which have been used therapeutically for millennia in Asia and Africa. The action of psoralens and light has been used to treat vitiligo and psoriasis (PUVA therapy; Psoralen Ultra Violet A) and more recently various forms of lymphoma.

Psoralen will bind to nucleic acid double helices by intercalation between base pairs; adenine, guanine, cytosine and thymine (DNA) or uracil (RNA). Upon absorption of UVA photons the psoralen excited state has been shown to react with a thymine or uracil double bond and covalently attach to both strands of a nucleic acid helix.

The crosslinking reaction is specific for a thymine (DNA) or uracil (RNA) base and will proceed only if the psoralen is intercalated in a site containing thymine or uracil. The initial photoadduct can absorb a second UVA photon and react with a second thymine or uracil on the opposing strand of the double helix to crosslink the two strands of the double helix.

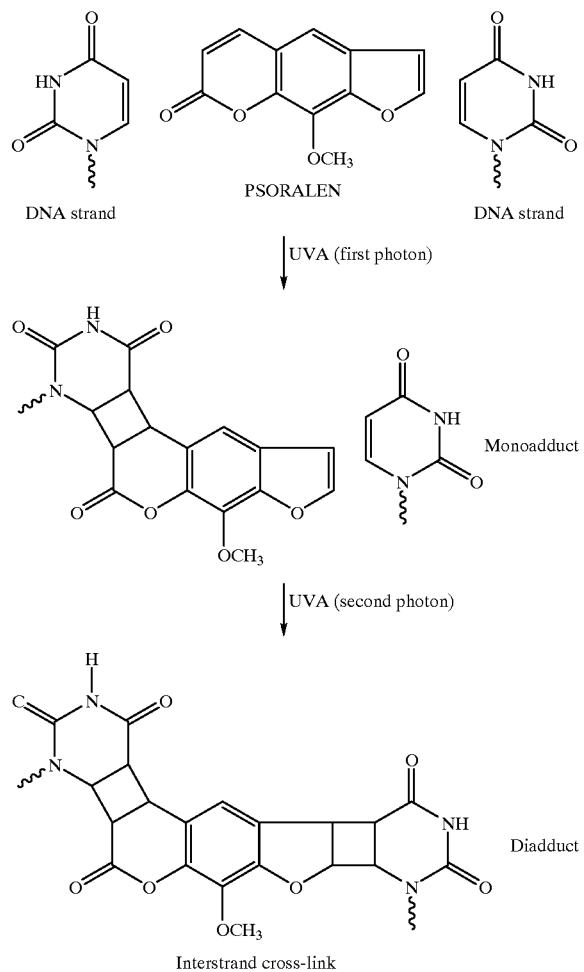

Lethal damage to a cell or virus occurs when a psoralen intercalated into a nucleic acid duplex in sites containing two thymines (or uracils) on opposing strands sequentially absorb 2 UVA photons. This is an inefficient process because two low probability events are required, the localization of the psoralen into sites with two thymines (or uracils) present and its sequential absorption of 2 UVA photons.

U.S. Pat. No. 4,748,120 of Wiesehan is an example of the use of certain substituted psoralens by a photochemical decontamination process for the treatment of blood or blood products. The psoralens described for use in the process do not include halogenated psoralens, or psoralens with non-hydrogen binding ionic substituents. Using traditional psoralens such as 8-MOP, AMT and HMT, it is imperative that additives be added into the blood product solution in conjunction with UV irradiation in order to scavenge singlet oxygen and other highly reactive oxygen species formed by irradiation of the psoralen. Without the addition of reactive oxygen species scavengers, cellular components and protein components in the blood product are seriously damaged upon irradiation. (See also, U.S. Pat. No. 5,176,921.) It is clear, therefore, that irradiation of psoralens such as 8-MOP and AMT in aqueous solution creates a competition between the inefficient photocrosslinking reaction and the generation of highly reactive oxygen species. It is also possible that much of the viral deactivation seen using these photosensitizers actually results from the action of the reactive oxygen species against the viral contaminants rather than the inefficient photocrosslinking mechanism.

Whenever photoactivated techniques are relied on in any synthetic or deactivation process, it is critical to remember that it is extremely rare when the introduction of energy into a molecular chromophore results in a single chemical pathway for dissipation of the energy. The result of this dilemma in this particular area of research is 1) that the mechanism for viral inactivation can take a variety of pathways, and 2) that unwarranted and unanticipated side reactions may occur.

As described in previous applications commonly owned with this application, some of the best compounds for use in photo-assisted viral inactivation have a psoralen or coumarin backbone. These compounds are nucleic acid intercalators, and thus assure that the photosensitizer associates with the nucleic acid of viral or bacterial contaminants in biological solutions. Unfortunately, it has been shown that the use of psoralen and coumarin photosensitizers can give rise to alternative chemical pathways for dissipation of the excited state that are either not beneficial to the goal of viral inactivation, or that are actually detrimental to the process. For psoralens and coumarins, this chemical pathway is likely to lead to the formation of a variety of ring-opened species. FIG. 1 depicts the possible structure of several ring-opened species that may result from the inactivation of a coumarin photosensitizer. Similar types of ring-opened species can be envisioned as arising from the inactivation of psoralen backbone photosensitizers.

The formation of non-productive reaction products upon irradiation leads to two concerns. The first concern is related to the toxicity of byproducts formed, and the second concern is the further reactivity of such byproducts. Additional reactions to the byproducts can either be photo assisted or simply due to the highly reactive nature of the compounds.

Considering the complexity of a system that includes, for example, red blood cells and a photosensitizer that is irradiated, it is naturally impossible to pinpoint all the modes of reaction that will lead to successful viral inactivation as opposed to detrimental surface modification of the red blood cells. Researchers in this field have typically been guilty of over-simplifying the claimed mechanisms involved in such a complex system. Many in the field believe that psoralen irradiation leads to viral irradiation strictly by the photoactivating mechanism described above. Others have speculated that the formation of highly reactive oxygen species such as singlet oxygen actually are the species that leads to both viral inactivation and cell surface modification.

The complexity of these systems is only recently being fully appreciated by researches searching utilizing photosensitizers for viral inactivation processes:

Unfortunately it is particularly rare to find photo chemical agents that undergo a single type of chemical reaction. Nearly all photosensitizers that produce singlet oxygen are capable, at least in principle, of undergoing a number of other types of reactions, such as direct attack of the sensitizer-excited states on substrates or formation of radicals, especially in the complex mixtures of compounds characteristic of living systems. (Chapter 4 in "Psoralen DNA Photobiology, Vol. II, F. P. Gasparro, ed. 1988).

Despite this recognition, and the obvious fact that the nature of the causative agents that damage cells and proteins during irradiation is not known, the prior art tends to focus on singlet oxygen and the use of antioxidant quenchers. What is needed is a "blocking" agent that will serve to block deleterious cell or protein damage independent of the claimed reaction that leads to the damage.

U.S. patent application Ser. Nos. 07/510,234 filed Apr. 16, 1990 and 07/686,334 filed Apr. 16, 1991—both incorporated herein by this reference—describe a novel photosensitizer utilizing the quinolone backbone. It is speculated that the use of photosensitizers with the quinoline or quinolone backbone will be less susceptible to ring opening side reactions upon irradiation.

Attempts to inactivate viral decontaminants using photosensitizers and light have also been developed using some non-psoralen photosensitizers. The photosensitizers that have been employed are typically dyes. Examples include dihematoporphyrin ether (DHE), Merocyanine 540 (MC540) and methylene blue.

In any event, an effective radiation photosensitizer must bind specifically to nucleic acids and must not accumulate in significant amounts in lipid bilayers, which are common to viruses, erythrocytes, and platelets. Although there is evidence that psoralens bind to nucleic acids by intercalation, neutral psoralens such as 8-MOP (8-methoxypsoralen) are uncharged and thus also have a high affinity for the interior of lipid bilayers and cell membranes.

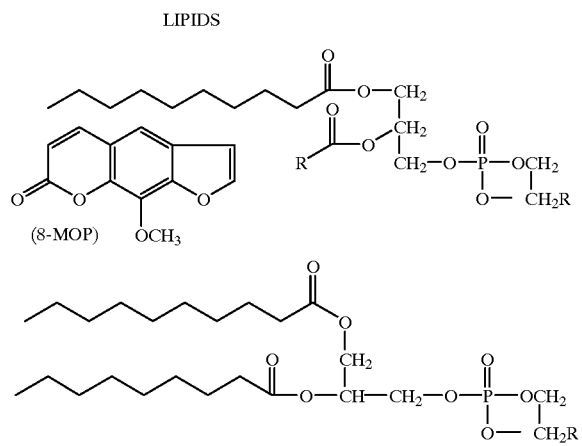

The binding of 8-MOP to cell membranes, shown above, would be acceptable if the psoralen bound to the lipid was photochemically inert. However, Midden (W. R. Midden, Psoralen DNA photobiology, Vol II (ed. F. P. Gaspalloco) CRC press, pp. 1. (1988) has presented evidence that psoralens photoreact with unsaturated lipids and photoreact with molecular oxygen to produce active oxygen species such as superoxide and singlet oxygen that cause lethal damage to membranes. Thus, it is believed that 8-MOP is an unacceptable photosensitizer because it sensitizes indiscriminate damage to both cells and viruses.

Positively charged psoralens such as AMT (4'-aminomethyl-4,5',8-trimethylpsoralen) will not bind to the interior of phospholipid bilayers (membranes) because of the presence of the charge. However, AMT contains an acidic hydrogen which can bind to the phospholipid head group by hydrogen bonding, shown below.

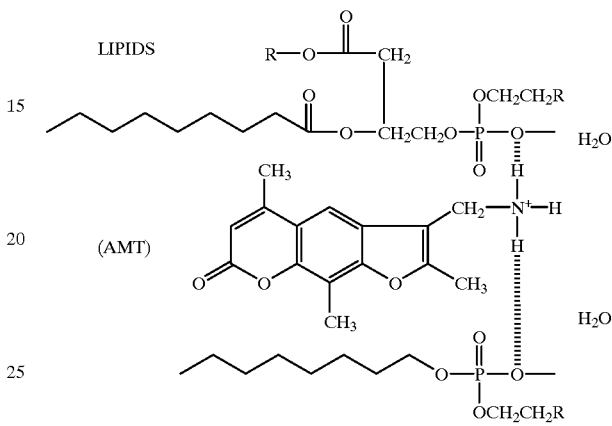

Thus AMT is believed to be an unacceptable photosensitizer because it will indiscriminately sensitize damage to viral membranes and to the membranes of erythrocytes and platelets.

Studies of the affects of cationic sidechains on furocoumarins as photosensitizers are reviewed in Psoralen DNA Photobiology, Vol. I, ed. F. Gaspano, CRC Press, Inc., Boca Raton, Fla., Chapter 2. The following points can be gleaned from this review:

1) The intent of this line of research was to improve the poor water solubility of the basic psoralen nucleus.

2) None of the psoralens described were halogenated as are the photosensitizers of the present invention.

4) Later conducted studies showed that a cationic group on a large linker, when added to the 5 or 8 position on the psoralen ring, gave the psoralen nucleus improved binding with native DNA relative to corresponding 5-MOP and 8-MOP analogues.

5) Sidechain substitution at the 5 position was found to be less desirable then substitution at the 8 position.

6) A study of 5-aminomethyl derivatives of 8-MOP showed that most of the amino compounds had a much lower ability to both photobind and form crosslinks to DNA compared to 8-MOP. These reports actually suggest that the primary amino functionality is the preferred ionic species for both photobinding and crosslinking.

U.S. Pat. No. 5,216,176 of Heindel describes a large number of psoralens and coumarins that have some effectiveness as photoactivated inhibitors of epidermal growth factor. Included among the vast functionalities that could be included in the psoralen or coumarin backbone were halogens and amines. The inventors did not recognize the significance of either functionality or the benefits of a photosensitizer including both functionalities.

U.S. patent applications Ser. Nos. 08/165,305 and 08/091,674 are commonly assigned with the present application, and are parent applications to this application. These applications disclose the use of a novel class of psoralen photosensitizers that are superior for use with irradiation to inactivate viral and bacterial contaminants in blood and blood products. The psoralens are characterized by the presence of a halogen substituent and a non-hydrogen binding ionic substituent to the basic psoralen side chain. See also, Goodrich et al. Proc. Natl. Acad. Sci. USA, 91:5552–56 (1994).

SUMMARY OF THE INVENTION

The present invention provides a method for the inactivation of viral and bacterial contaminants present in blood and blood protein fractions.

The present invention involves utilization of photosensitizers which bind selectively to a viral nucleic acid, coat protein or membrane envelope. The photosensitizer is also a moiety which can be activated upon exposure to radiation, which may be in the form of ultra-violet radiation or ionizing radiation, such as X-rays, which can penetrate the sample containing the contamination.

The present invention is also applicable to inactivation of blood-borne bacterial contaminants, and to blood-borne parasitic contaminants, since such infectious organisms rely on nucleic acids for their growth and propagation. Since purified blood plasma protein fractions are substantially free of human nucleic acids, and mature human peripheral blood cells, particularly red blood cells and platelets lack their own genomic DNA/RNA, the use of nucleic acid-binding photosensitizers is especially useful for the problem of treating blood contaminants.

The present invention may also be applied to viral inactivation of tissues and organs used for transplantation, and used in topical creams or ointments for treatment of skin disorders or for topical decontamination. The present invention may also be used in the manufacture of viral vaccines for human or veterinary use, particularly to produce live, nonviable or attenuated viral vaccines. The present invention may also be used in the treatment of certain proliferative cancers, especially solid localized tumors accessible via a fiber optic light device or superficial skin cancers.

The present invention includes the utilization of a class of compounds that have a selective affinity to nucleic acid. The class of compounds also contains a halogen substituent and a water solubilization moiety, such as, quaternary ammonium ion or phosphonium ion. These materials comprise a relatively low toxicity class of compounds, which can selectively bind to the nucleic acid (single-stranded DNA, double-stranded DNA, or RNA) that comprises the genetic material of viruses. The bound compound can be activated by exposure to radiation, such as ultraviolet radiation (UV light of a defined wavelength), or ionizing radiation such as x-rays, after which the activated compound damages the bound viral nucleic acid or viral membranes rendering the virus sterile and non-infectious. Activation of the selectively bound chemical photosensitizer focuses the photochemistry and radiation chemistry to the viral nucleic acid or viral membranes and limits exposure to nearby cellular components or plasma proteins.

The preferred class of photosensitizers for use with the present invention are characterized generally as follows: a) they are intercalators, and they are comprised of either b) at least one halogen substituent or c) at least one non-hydrogen bonding ionic substituent. In preferred embodiments the photosensitizers comprise at least one halogen substituent and at least one non-hydrogen bonding ionic substituent. Particularly preferred photosensitizers are psoralens and coumarins comprising at least one halogen substituent and at least one non-hydrogen bonding ionic substituent.

The photosensitizers disclosed herein are suited for the inactivation of a variety of viral and bacterial contaminants associated with blood and blood products. The present invention specifically includes the photoinactivation of blood and blood products contaminated with Human Immunodeficiency Virus-1 (HIV-1), Sindbis virus, Cytomegalovirus, Vesicular Stomatitis Virus (VSV), and Herpes Simplex Virus Type 1 (HSV-1), using the photosensitizers of the present invention.

The present invention also demonstrates the flexibility of adding one or more halogen atoms to any cyclic ring structure capable of intercalation between the stacked nucleotide bases in a nucleic acid (either DNA or RNA) to confer new photoactive properties to the intercalator. In the present invention essentially any intercalating molecule (psoralens, coumarins, or other polycyclic ring structures) can be selectively modified by halogenation or addition of non-hydrogen bonding ionic substituents to impart advantages in its reaction photochemistry and its competitive binding affinity for nucleic acids over cell membranes or charged proteins.

In one embodiment, halogenation of psoralen enables the molecule, once intercalated within the nucleic acid, to undergo a strand cleavage reaction upon light activation that non-halogenated psoralens cannot initiate. The nucleic acid strand cleavage is due to a novel electron transfer pathway created by the breaking of the carbon-halogen bond upon input of appropriate radiation energy. The mechanism for this alternate chemical reaction requires a single photon of light and is more efficient than the crosslinking reaction that normally occurs with non-halogenated psoralens. In addition, the electron transfer reaction involves transfer from a donor (usually a guanine base when the intercalator is inserted in nucleic acid) and an acceptor (the carbon radical created by breakage of the carbon-halogen atom). Since the donor and acceptor species must be in close physical proximity for the transfer reaction to proceed, most damage is limited to the nucleic acid as desired for viral inactivation.

In a second embodiment, halogenation of a coumarin imparts totally new photoactive properties useful for viral inactivation. Coumarins, unlike psoralens, do not have an inherent ability to crosslink nucleic acid strands upon exposure to radiation, and hence have not heretofore found application as photosensitizers. However, as shown in the present invention, halogenation of this class of intercalating molecules confers the ability to undergo the electron transfer mechanism, thereby imparting new properties to the molecule. Without intending to limit the present invention, the inventors believe that the example of coumarin halogenation demonstrates that these principles can be extended to any intercalating molecule, to confer new photoactive properties.

Due to the flexibility in adding halogen substituents or non-hydrogen bonding ionic substituents to virtually any cyclic or polycyclic ring structure, the inventors envision that new and useful molecules can be created by adapting the present invention to many known classes of ring compounds, whether those compounds comprise intercalating agents or not. For example, known classes of compounds that may be improved by the present invention include, porphyrins, phthalocyanines, quinones, hypericin, and many organic dye molecules (such as coumarins) including merocyanine dyes, methylene blue, eosin dyes, and others.

Without intending to limit the present invention, the inventors anticipate that new classes of compounds prepared according to the principles of this invention will find application in numerous fields in addition to decontamination of blood and blood products. The new chemical reaction properties imparted by halogenation and the selective binding properties imparted by the use of non-hydrogen bonding ionic substituents, may be grafted onto known classes of molecules to impart advantageous chemical reaction and targeting properties to these molecules. Psoralens for example, such as 8-methyoxypsoralen (8-MOP) have been used in therapeutic photophoresis to treat cutaneous T-cell lymphoma, scleroderma, and other cancers or skin disorders. The modified psoralen derivatives of the present invention (or other classes of compounds modified according to the present invention) may prove more efficacious in therapeutic photophoresis applications.

As a second example, organic dyes such as methylene blue (which is not considered a nucleic acid intercalating compound) have been used for viral inactivation treatments of blood plasma, with questionable success. It is contemplated that such organic dyes, modified according to the present invention, may prove more efficacious in such an application than the unmodified dye.

In one embodiment of the present invention the photosensitizers of the present invention are irradiated in the presence of a "blocking" agent. The blocking agent is a chemical that is capable of reducing deleterious side reactions such as cell surface modifications or protein modifications. Of particular concern are the blocking of deleterious side reactions that are a result of irradiation-induced reactions to the photosensitizers that do not result in viral or bacterial inactivation. More specifically, of concern are reactions that occur to psoralen and coumarin backbone photosensitizers upon irradiation; presumably these reactions lead to ring-opened species that are highly reactive.

A variety of blocking agents have been found to be suitable for this purpose, some of which are traditional antioxidants, and some of which are not. In the preferred embodiments of the invention the blocking agent is cysteine and in the most preferred embodiment the blocking agent is N-acetyl-L-cysteine.

The present invention, therefore, includes a method for inactivating viral and bacterial contaminants from a biological solution comprising mixing said biological solution with a photosensitizer and a blocking agent and irradiating said mixture under conditions whereby substantially all of said contaminants are inactivated and the physiological activity of said biological solution is substantially unimpaired. According to this method, the photosensitizer upon irradiation participates in deleterious side reactions when not in the presence of said blocking agent that are not exclusively or predominantly the result of reactive oxygen species, and the mode of action of the blocking agent is not predominantly in the quenching of reactive oxygen species.

The present invention also includes an additional novel family of photosensitizers. The defining characteristic of their new family of photosensitizers is a chemical backbone of quinoline or quinolone. It has been shown that such photosensitizers, modified in a variety of different ways, leads to the viral inactivation of biological solutions with reduced damage to the physiological functions of the biological solution.

The present invention includes, therefore, a method for inactivating viral and bacterial contaminants from a biological solution comprising mixing said biological solution with a photosensitizer, wherein said photosensitizer is a quinoline or quinolone, and irradiating said mixture under conditions whereby substantially all of said contaminants are inactivated and the physiological activity of said biological solution is substantially unimpaired.

Other fields of application wherein the present invention may find application include the preparation of non-infectious viral vaccines, therapeutic treatment of immune system disorders by photophoresis, elimination of viable nucleated cells such as leukocytes via the cytotoxicity of nucleic acid binding photosensitizers, and possible treatment for certain accessible cancers and tumors, again exploiting the cytotoxic effects of nucleic acid binding photosensitizers.

BRIEF DESCRIPTION OF THE DRAWINGS

FIG. 8 shows HPLC chromatograms of a solution containing Photosensitizer A following irradiation alone (FIG. 8A) and in the presence of 10 mM N-acetyl-L-cysteine (FIG. 8B).

DETAILED DESCRIPTION OF THE INVENTION

Figure 1:
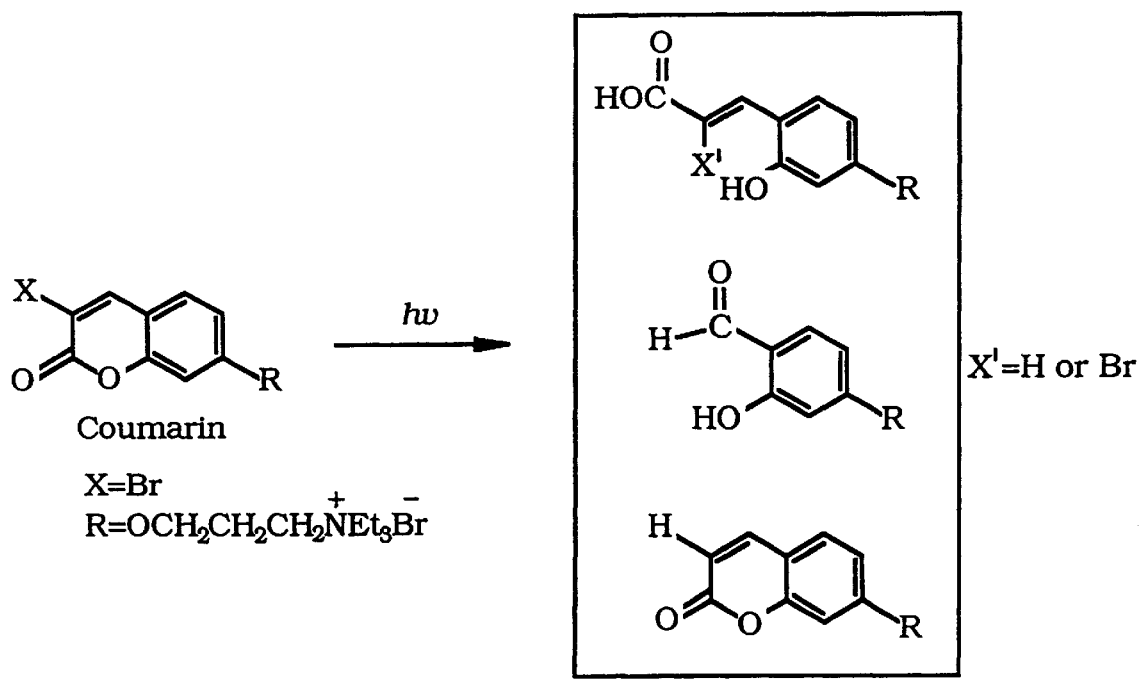
FIG. 1 depicts the potential photo products resulting from the irradiation of Photosensitizer A.

The present invention is directed to methods for reducing viral, bacterial and other parasitic contamination in blood, blood components, cell cultures or cell culture components by irradiation in the presence of a chemical photosensitizer. Photosensitizers are disclosed which are particularly useful to decontaminate liquid compositions, such as blood, blood components, reconstituted lyophilized cells, and the like, using UV irradiation.

According to the present invention, a radiation sensitizing chemical compound is added to a liquid suspension of infectious viruses and/or bacteria and/or parasites, and the mixture is exposed to UV light or ionizing radiation. Assays of viral infectivity demonstrate the effectiveness of the compounds to inactivate the viruses, compared to radiation treatment alone.

The present invention includes a method for reducing viral, bacterial and other parasitic contamination from a biological solution. Biological solutions include, but are not limited to, solutions comprising blood, a blood component, cell culture or a component of a cell culture. The method comprises mixing the composition in a liquid state with a photochemical photosensitizer capable of binding to the viral, bacterial or parasitic contamination. The photochemical photosensitizer is capable of being activated by irradiation under conditions of sufficient wavelength, intensity and period of exposure to inactivate the contaminant, while at the same time the conditions for irradiation are insufficient to produce reactive oxygen species in the composition at levels which substantially impair the physiological activity of the treated composition. The composition containing the photosensitizer is then irradiated under conditions where the concentration of biologically active contaminant is reduced and the physiological activity of the composition is substantially unimpaired.

In one embodiment of the invention, one of the most critical elements is the use of a novel class of photosensitizer. A photosensitizer is defined for the purposes of this application as a chemical compound that has a light-absorbing chromophore that absorbs radiation in the ultraviolet or visible spectrum, and that is capable of inactivating viral or bacterial contaminants in blood or blood products.

The photosensitizers of the present invention are characterized by their ability to bind to the nucleic acid components of the viral or bacterial contaminants that are to be inactivated. The blood and blood product compositions that are to be treated according to the method of this invention all contain at least some cellular components or complex proteins.

In one embodiment of the invention, the photosensitizers of this invention are characterized as comprising a lipophilic moiety, a hydrophilic moiety and a photoreactive moiety.

Photosensitizers included in this invention are preferably nucleic acid intercalators that are comprised of either 1) at least one halogen atom; and 2) at least one non-hydrogen bonding ionic moiety. Intercalators are defined broadly herein as any chemical compound that has a specific affinity to double or single stranded nucleic acid. More specifically, intercalators are chemicals—not including nucleic acids, proteins or peptides—that locate themselves between neighboring base pairs in nucleic acids. Intercalators are generally characterized by the presence of a relatively planar rigid, multi-cyclic pi-conjugated chemical backbone. Those skilled in the art are familiar with a relatively large number of intercalators, and are generally able to predict the types of chemical species that are able to function as intercalators based on the chemical structure of the backbone of the chemical species. Psoralens and coumarins, which are two of the preferred basic structures for the intercalators of the present invention, are just two examples of chemical backbone structures capable of nucleic acid intercalation.

Certain preferred photosensitizers of the present invention comprise at least one halogen substituent. The halogens include F, Cl, Br and I. In the preferred embodiments of the present invention, the photosensitizer contains at least one bromine or chlorine atom.

Certain preferred photosensitizers of the present invention comprise at least one non-hydrogen bonding ionic substituent. Chemical functionalities that are ionic and non-hydrogen bonding include quaternary ammonium functionalities and phosphonium functionalities. A variety of additional functionalities that are both ionic and non-hydrogen bonding are familiar to those skilled in the art, and equally applicable for use with this invention.

In certain preferred embodiments of the invention, the non-hydrogen bonding ionic substituent is linked to the backbone of the chemical intercalator via a spacer unit. The spacer can be selected from any of a number of chemical subunits known to those skilled in art, but in the preferred embodiments is composed of a saturated linear alkoxy group. In the most preferred embodiment the spacer element is —O(CH$_2$)$_3$—.

The most preferred non-hydrogen bonding ionic functionalities are quaternary ammonium functionalities, more specifically trialkyl quaternary ammonium and even more specifically —O(CH$_2$)$_3$ N$^{\oplus}$(CH$_2$CH$_3$)$_3$.

Two preferred photosensitizers of the present invention are the following:

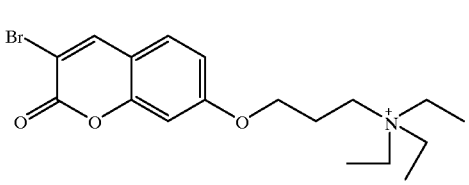

A

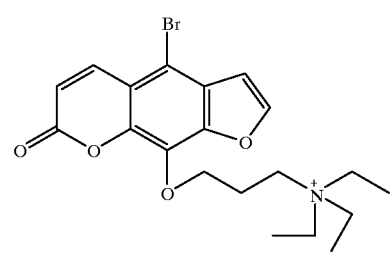

B

Compound A is a coumarin based photosensitizer, and compound B is a psoralen or furocoumarin based photosensitizer.

Additional preferred embodiments of the present invention include the following coumarin based photosensitizers:

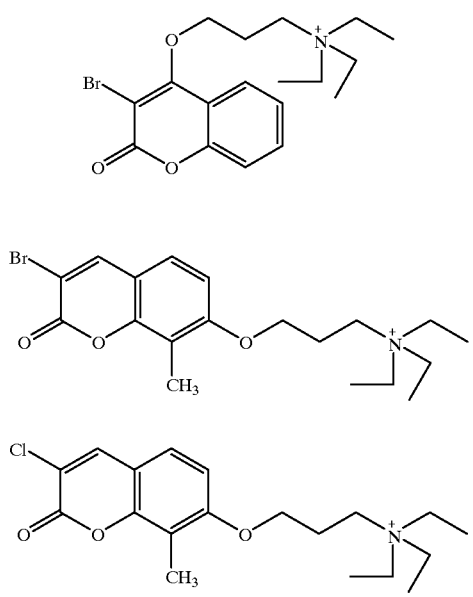

The synthesis of Photosensitizer A and Photosensitizer D is described in copending U.S. patent application Ser. No. 08/343,680 filed Nov. 22, 1994, incorporated herein by reference.

Upon irradiation with UV light, compound A has been shown to be effective at viral inactivation while compound B has been shown to be effective at viral and bacterial inactivation. Compounds A, D and E also fluoresce upon UV irradiation. It is theorized by the present inventors that the fluorescence pathway for the dispersion of energy from the excited state of irradiated compounds A, D and E acts to reduce the production of highly reactive oxygen species in blood and blood components. According to the proposed mechanism—which is speculative and not intended to limit the scope of the invention—the photoreaction is initiated by an electron transfer from a guanine residue to the photosensitizer in its executed singlet state. Electron transfer is followed by halo-C bond homolysis and the generation of a coumarin radical that can attack the nucleic acid backbone.

Bromopsoralens, and Photosensitizer B specifically, do not form free radicals upon irradiation in solution. A donor is required to activate Photosensitizer B. Using fluorescence spectroscopy it has been shown that amino acids are not suitable donors to activate Photosensitizer B. Thus any of these photosensitizers bound or associated with proteins should not generate radicals capable of damaging proteins.

It is therefore one preferred embodiment of the method of the present invention to use a photosensitizer that is capable of fluorescence. Coumarins and furocoumarins that fluoresce are known to those skilled in the art, and the screening of photosensitizers to determine fluorescent properties is easily determined.

Photosensitizers that are capable of fluorescence appear to be superior to non-fluorescent varieties. For a photosensitizer to be useful, there must be a mechanism for viral and bacterial inactivation. Non-halogenated psoralens may still function as useful photosensitizers if they are properly situated in the solution to be treated. Such compounds can inactivate viruses via the traditional photocrosslinking mechanism. Other photosensitizers, such as those having the coumarin backbone structure, must be halogenated in order to accomplish significant viral or bacterial inactivation.

Thus, in this embodiment of the invention the preferred photosensitizers are intercalators, are capable of fluorescence; and either 1) are halogenated; or 2) have the psoralen backbone structure.

The quaternary ammonium or phosphonium substituted halo-intercalators described herein do not accumulate in the interior of lipid bilayers (membranes) found in blood and blood products because of the presence of the charge, nor will they bind to the phospholipid head groups of the membrane because they lack acidic hydrogen for hydrogen bonding.

One preferred class of photosensitizers is selected from the group consisting of compounds of the formula (I):

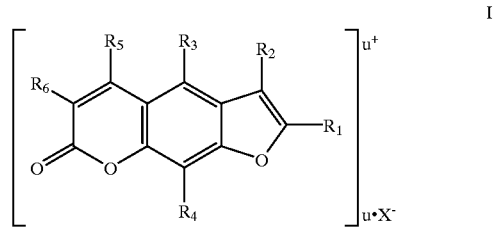

wherein u is an integer from 1 to 6; X is an anionic counterion; Z is N or P; $R_1$, $R_2$, $R_3$, $R_4$, $R_5$, and $R_6$ are independently halo; H; linear or branched alkyl of 1–10 carbon atoms; linear or branched alkoxy of 1–10 carbon atoms; $(CH_2)_m$—$O(CH_2)_p Z^\oplus R'R''R'''$ or —$O(CH_2)_n Z^\oplus R'R''R'''$ wherein n, m and p are independently integers from 1 to 10 and R', R'', and R''' are independently H or linear or branched alkyl of 1 to 10 carbon atoms with the proviso that on each Z atom, not more than two of R', R'', or R''' may be H; and at least on one of $R_1$, $R_2$, $R_3$, $R_4$, $R_5$ or $R_6$ is $(CH_2)_m O(CH_2)_p Z^\oplus R'R''R'''$ or —$O(CH_2)_n Z^\oplus R'R''R'''$. Particularly preferred are compounds wherein $R_4$ is —$O(CH_2)_n N^\oplus R'R''R'''$, especially wherein R', R'' and R''' are ethyl and n=3. Preferably, $R_6$, $R_5$, $R_2$ and $R_1$ are hydrogen and $R_3$ is H or halo, preferably bromo.

An additional preferred class of photosensitizers is selected from the group consisting of the formula (II).

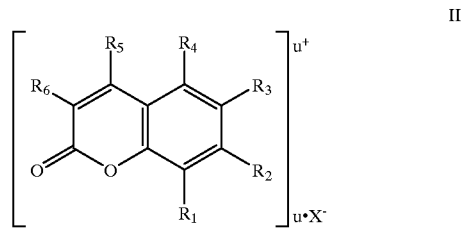

wherein u is an integer from 1 to 6; X is an anionic counterion; Z is N or P; $R_1$, $R_2$, $R_3$, $R_4$, $R_5$, and $R_6$ are independently halo; H; linear or branched alkyl of 1–10 carbon atoms; linear or branched alkoxy of 1–10 carbon atoms; $(CH_2)_m$—$O(CH_2)_p Z^\oplus R'R''R'''$ or —$O(CH_2)_n Z^\oplus R'R''R'''$ wherein n, m and p are independently integers from 1 to 10 and R', R'', and R''' are independently H or linear or branched alkyl of 1 to 10 carbon atoms with the proviso that on each Z atom, not more than two of R', R'', or R''' may be H; and at least on one of $R_1$, $R_2$, $R_3$, $R_4$, $R_5$ or $R_6$ is $(CH_2)_m O(CH_2)_p Z^\oplus R'R''R'''$ or —$O(CH_2)_n Z^\oplus R'R''R'''$. Particularly preferred are compounds wherein $R_4$ is —$O(CH_2)_n N^\oplus R'R''R'''$, especially wherein R', R'' and R''' are ethyl and n=3. Preferably, $R_3$, $R_5$, $R_2$ and $R_1$ are hydrogen and $R_3$ is H or halo, preferably bromo.

In general, the above compounds may be made by halogenating psoralens and isolating the appropriately substituted isomers. For compounds wherein the ring substituent is a quaternary ammonium alkoxy or phosphonium alkoxy group, that group may be made from the corresponding hydroxy-substituted psoralens, as exemplified by the following scheme.

compounds are capable of inactivating virus in biological solutions upon irradiation. This is true even for compounds that do not contain a halogen. In addition, it is not known that quinolines or quinolones will undergo crosslinking reactions with nucleic acids such as psoralens. Thus, the exact mechanism for light induced viral inactivation by such photosensitizers is not known.

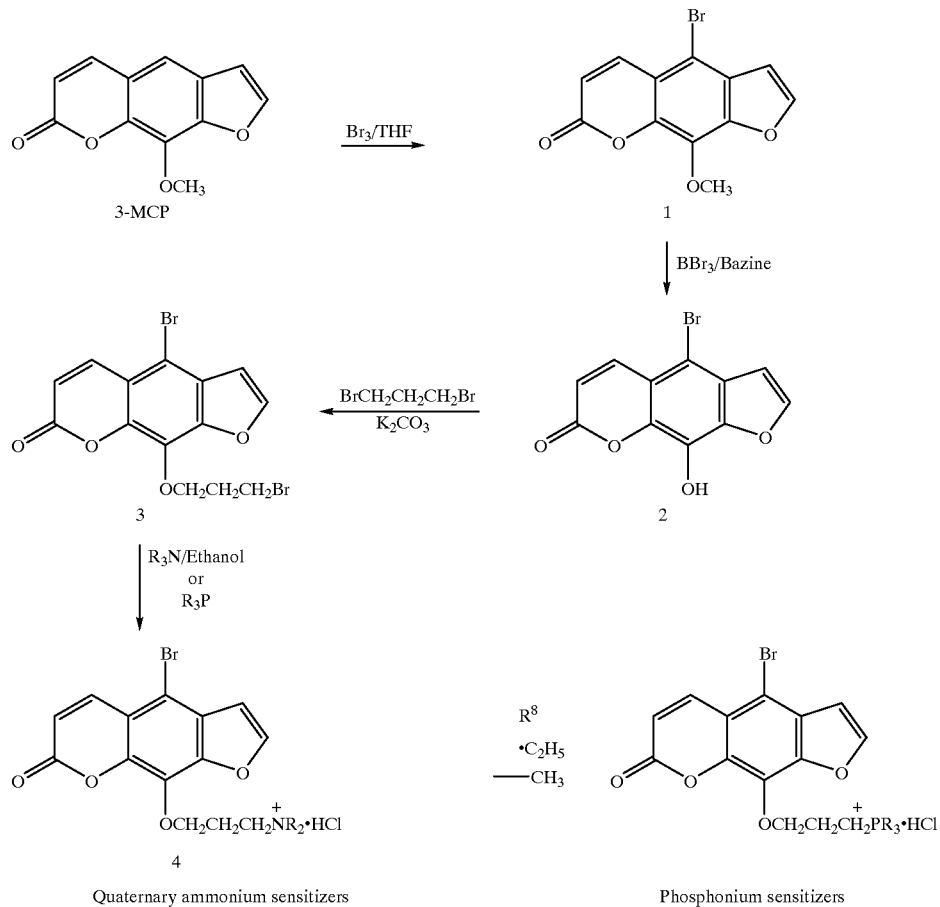

As described above, the most preferred photosensitizers of the present invention are comprised of ionic functionalities that are non-hydrogen bonding. However, included within the scope of this invention are photosensitizers comprised of amine functionalities having one and in some cases two amine hydrogens. These compounds, of course, are capable of forming hydrogen bonds. It has been shown that there is a direct correlation between the number of hydrogens available on the amine and the cellular destruction caused by a class of psoralen compounds. Goodrich, et al. Proc. Nat'l. Acad. Sci. USA, 91:5552–56 (1994). Thus, photosensitizers containing amine functionalities having two hydrogens are less preferred than those having one hydrogen, which are in turn less preferred than those having no hydrogen attached to the amine.

Therefore, according to this invention, sensitizing compounds for viral inactivation preferably do not contain substituents which possess free hydrogen groups capable of exhibiting hydrogen bonding to the cell membrane.

An additional novel class of photosensitizers useful in the present invention have either quinoline or quinolone backbone structures. It has surprisingly been shown that such

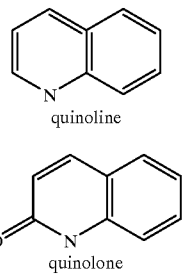

Included in this application are quinolines and quinolones modified in any manner.

Specifically included are photosensitizers of the structure:

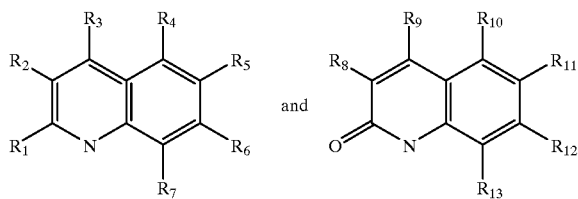

wherein $R_1$–$R_{13}$ are independently any chemical substituent, including but not limited to, halo, H, linear or branched or substituted alkyl of 1–15 carbon atoms, linear or branched or substituted alkoxy of 1–15 carbon atoms, any alkenyl ($C_1$–$C_{15}$), alkynyl ($C_1$–$C_{15}$) aryl, amino, thio, thioester, metal, silicon based substituent.

Certain preferred photosensitizers in this class included the following:

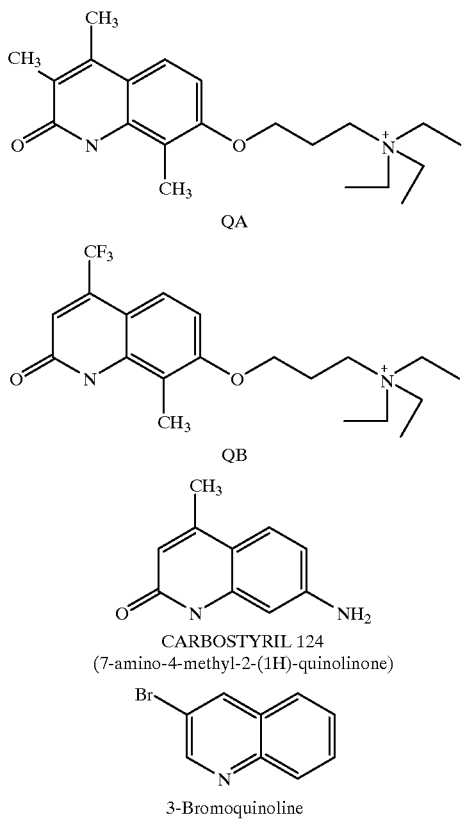

Based on previous work with cysteine blocking agents, and the analysis of the photolysis products obtained from both psoralen and coumarin sensitizers, quinolone and quinoline ring structures were looked at as possible intercalating agents. These two-ring compounds differ from the furocoumarins and coumarins in that the heteroatom in the rings incorporates the more stable nitrogen-carbon bond as opposed to the oxygen-carbon bond, which appears to be photolabile. Thus, it was predicted that the N-C ring compounds would be resistant to the kinds of ring-opening reactions by UV radiation observed with the coumarins and psoralens. Animal toxicology work comparing native Photosensitizer B and Photosensitizer A to their photobyproduct mixtures has shown in both cases that the photolysis products are more toxic than the parent molecules (data not shown). Thus, it is important from both a toxicity perspective and a cell quality perspective to minimize the kinds of photolysis reactions that we believe occur with these other photosensitizers.

Figure 9:
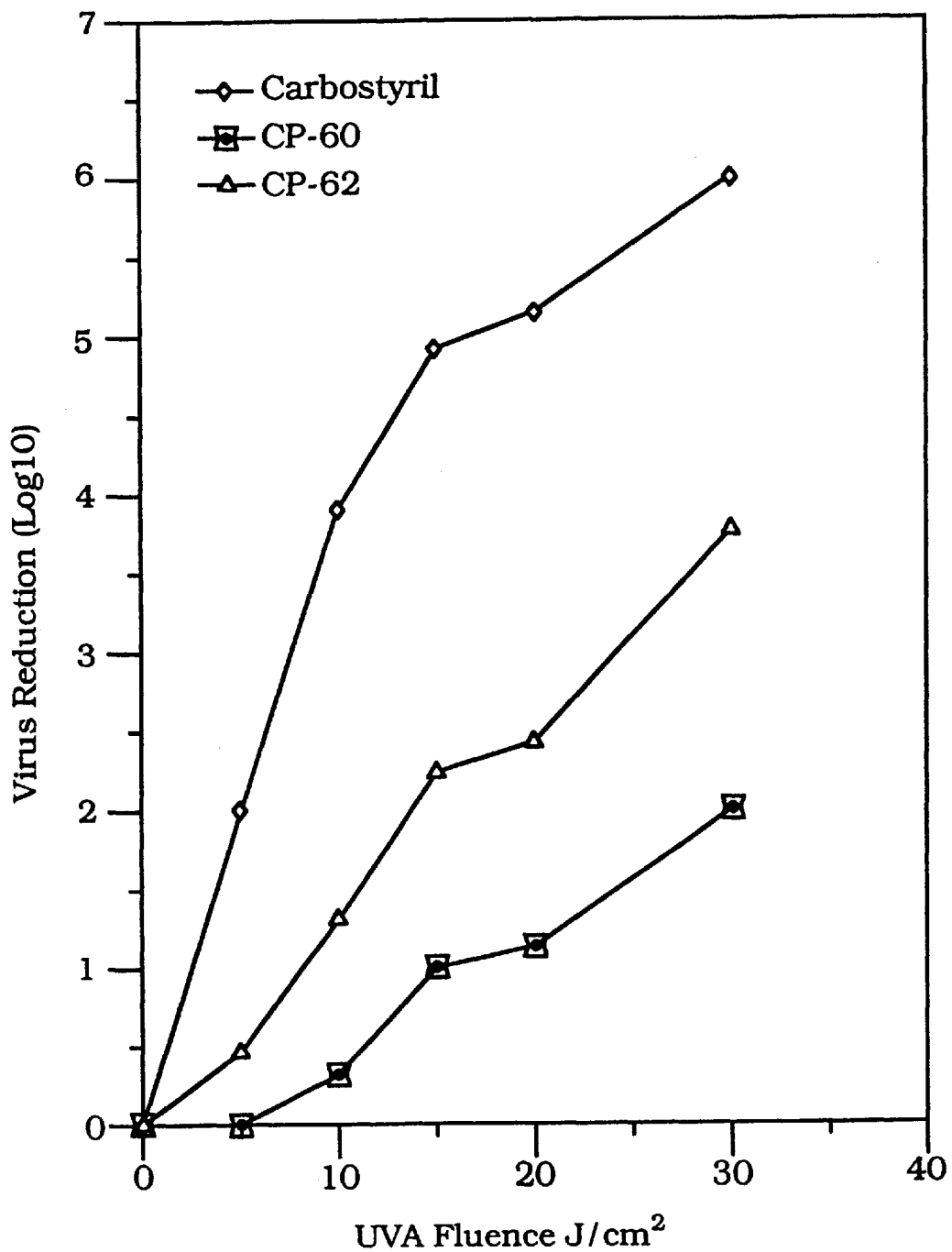
FIG. 9 is a plot showing the kinetics of inactivation of Sindbis virus using 300 $\mu$g/mL of Photosensitizer QA (-■-), QB (-▲-) and CARBOSTYRIL 124 (-◆-) in human plasma. The graph plots virus reduction versus UVA fluence.
Figure 10:
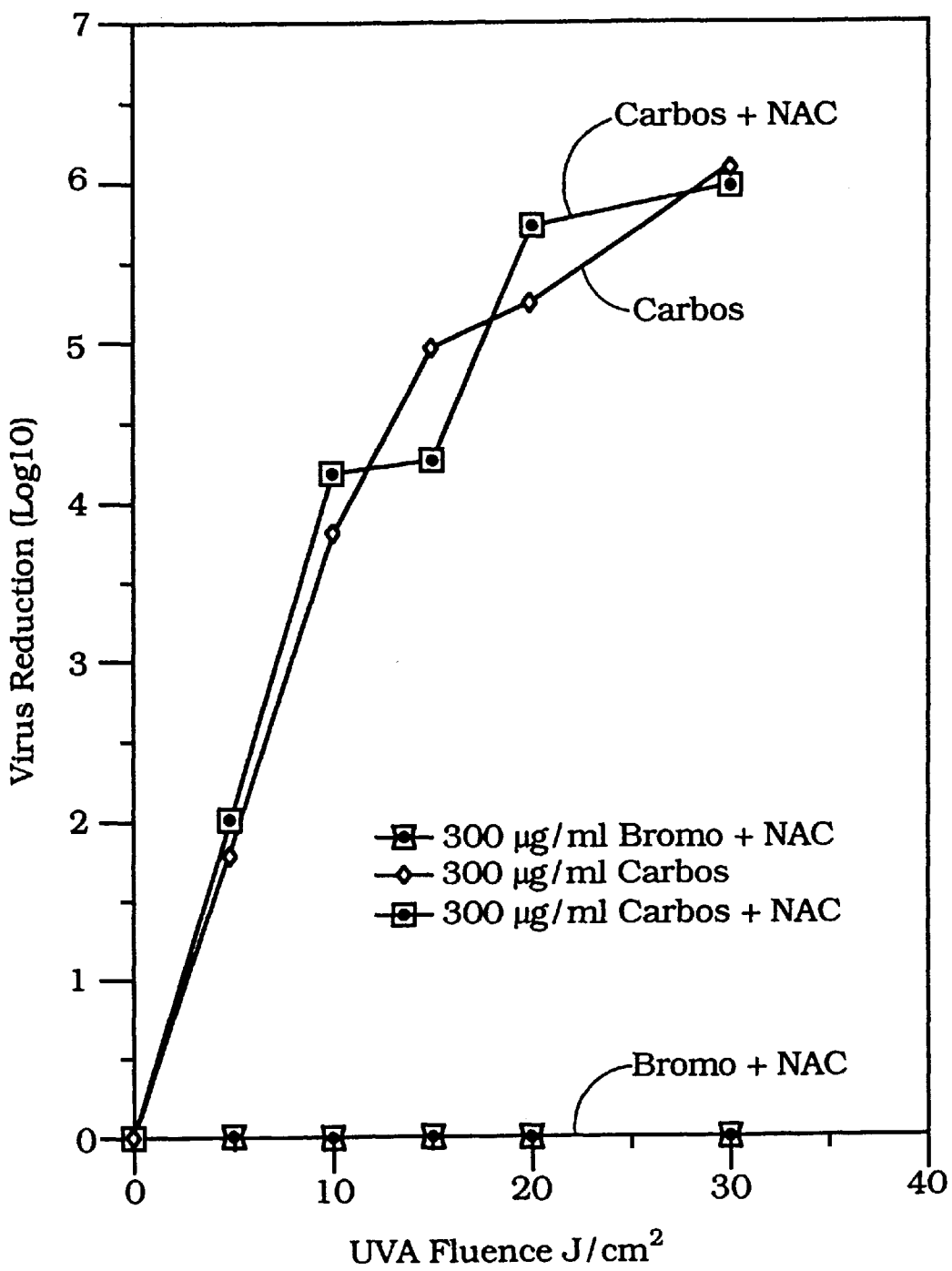
FIG. 10 is a plot showing the kinetics of inactivation of Sindbis virus using 300 $\mu$g/mL of bromoquinoline (-◆-), bromoquinoline and 10 mM N-acetyl-L-cysteine (-■-), CARBOSTYRIL 124 (-◇-), and CARBOSTYRIL 124 and 10 mM N-acetyl-L-cysteine (-□-). The graph plots virus reduction versus UVA fluence.

The experimental data below involves a study of viral inactivation of Sindbis virus using several quinolones (Photosensitizers QA and QB and CARBOSTYRIL 124; see FIG. 9). As shown in FIG. 9, the CARBOSTYRIL 124 compound was most effective against Sindbis virus seeded into human plasma and irradiated with UVA light. As shown in FIG. 10, CARBOSTYRIL 124 either with or without N-acetyl-L-cysteine is more effective against Sindbis virus than the 3-bromoquinoline, which appears to be relatively ineffective against Sindbis.

Figure 12:
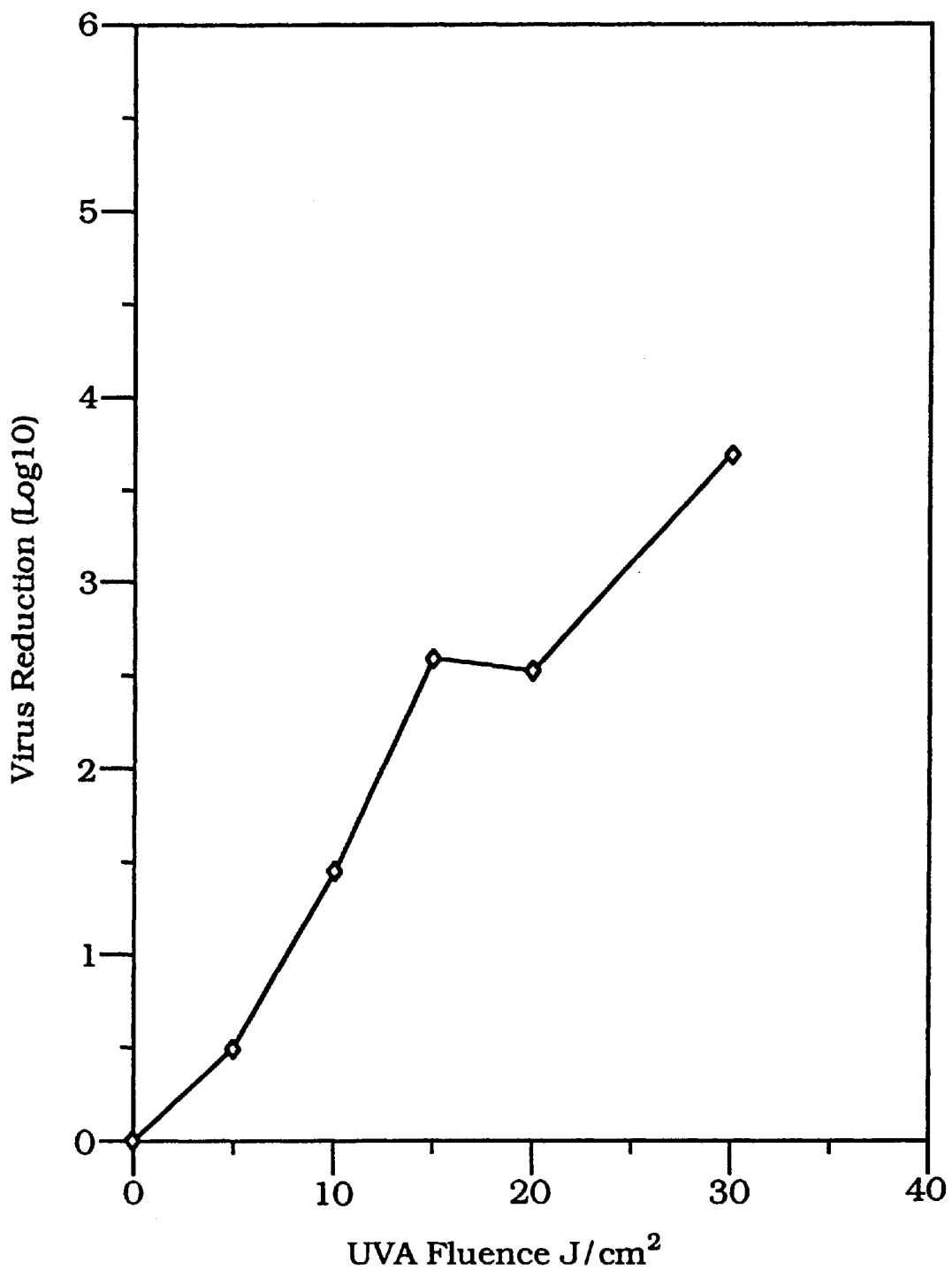
FIG. 12 is a plot showing the kinetics of inactivation of Sindbis virus using 16.7 $\mu$g/ml CARBOSTYRIL 124 with 10 mM N-acetyl-L-cysteine in plasma. The graph plots virus reduction versus UVA fluence.
Figure 13:
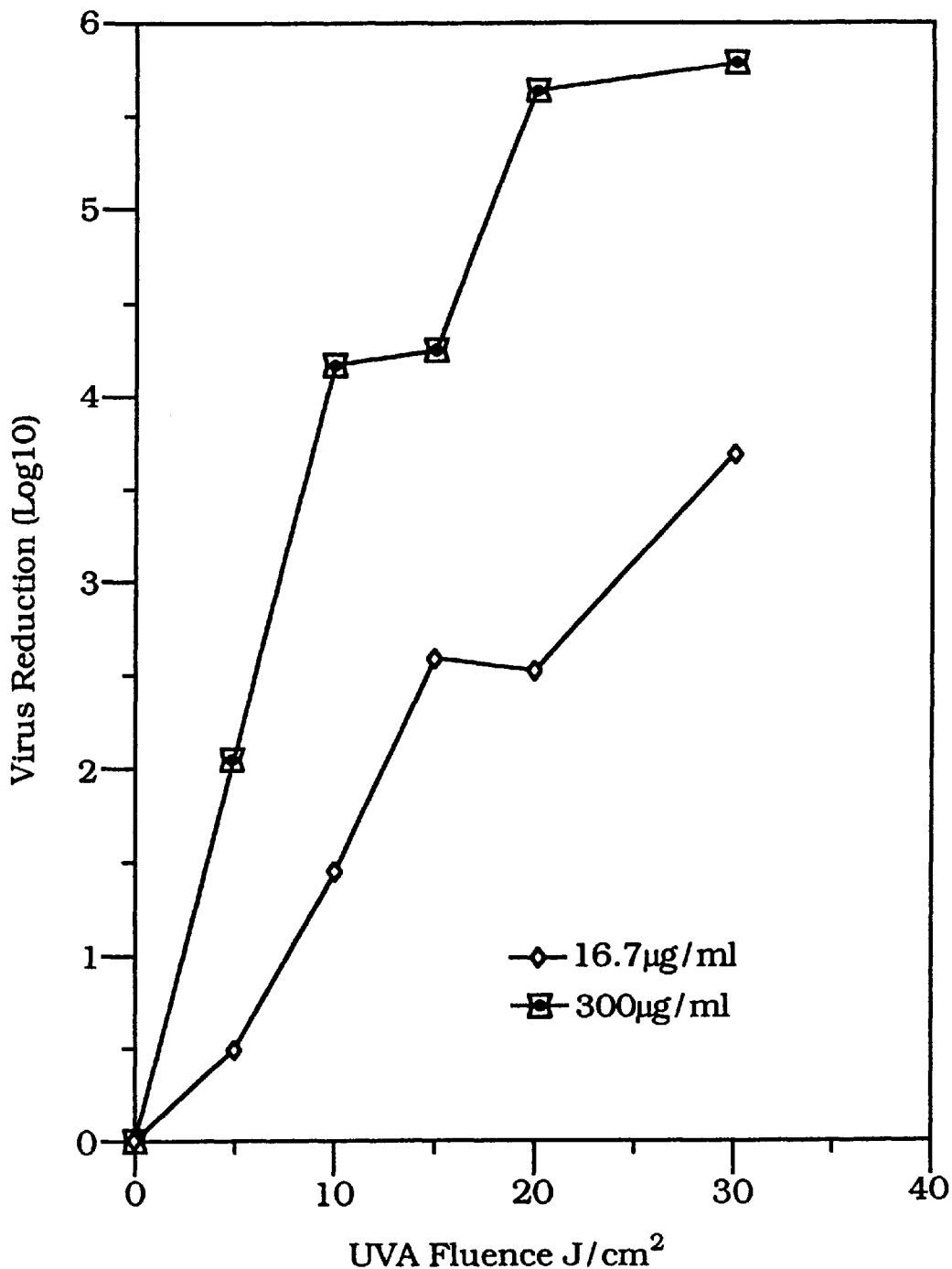
FIG. 13 is a plot showing the kinetics of inactivation of Sindbis virus using 16.7 $\mu$g/ml CARBOSTYRIL 124 (-◆-) and 300 $\mu$g/ml (-■-) with 10 mM N-acetyl-L-cysteine in plasma. The graph plots virus reduction versus UVA fluence.
Figure 14:
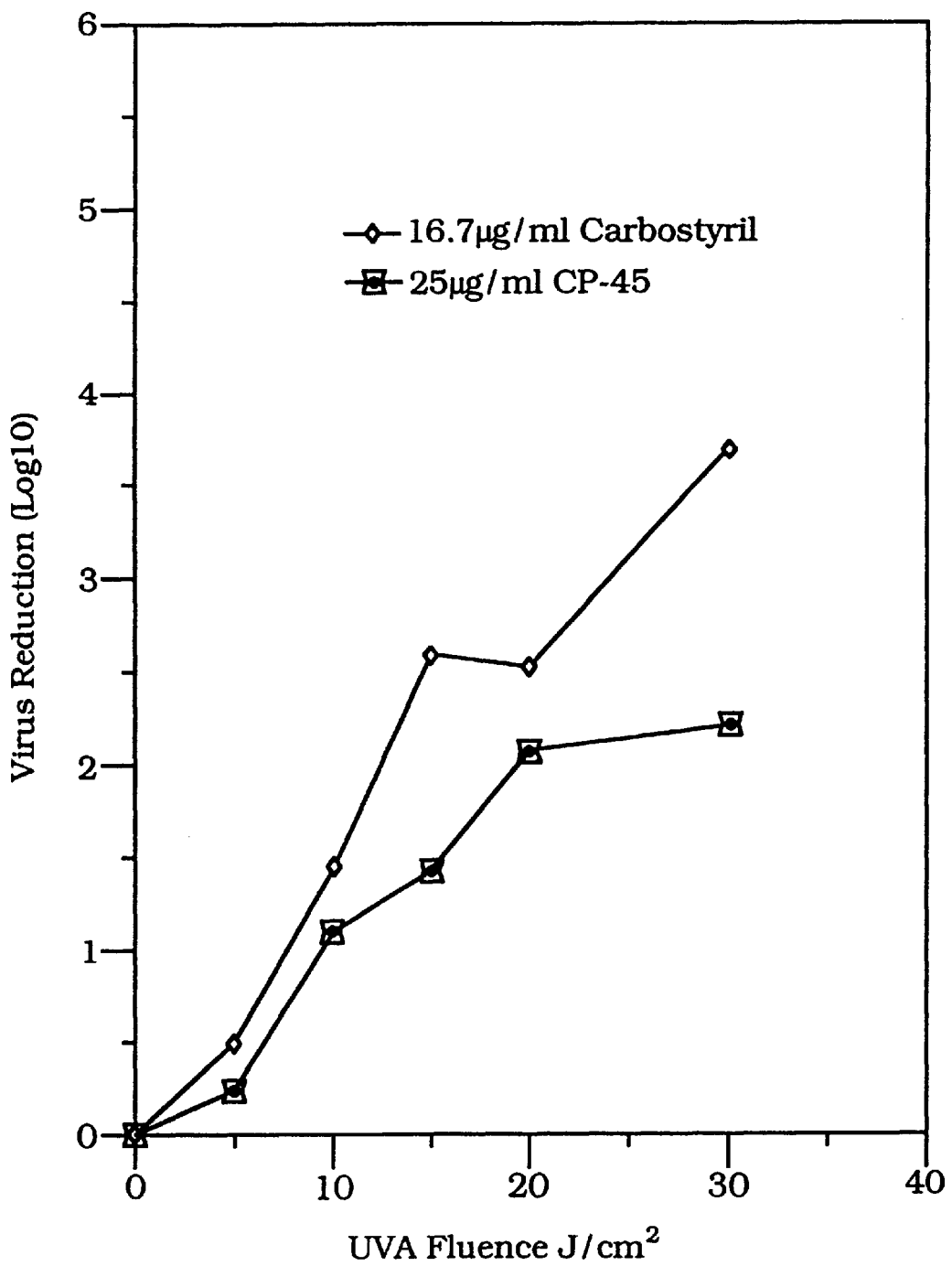
FIG. 14 is a plot showing the kinetics of inactivation of Sindbis virus using Photosensitizer A (-■-) or CAR- BOSTYRIL 124 (-♦-) with 10 mM N-acetyl-L-cysteine in plasma. The graph plots virus reduction versus UVA fluence.

The in vitro cell function assay data in Table 3 shows that CARBOSTYRIL 124 treated platelets exhibit some loss of function, particularly the aggregation response at 300 $\mu$g/mL CARBOSTYRIL 124 and 30 J/cm$^2$ light energy. Even at lower CARBOSTYRIL 124 concentration levels cells exhibit some loss of function. Table 5 shows platelet properties after CARBOSTYRIL 124 treatment with and without N-acetyl-L-cysteine. In spite of this decrease in cell function, FIGS. 12 and 13 illustrate that CARBOSTYRIL 124 with N-acetyl-L-cysteine inactivates Sindbis virus, by 4-fold, at a concentration of 16.7 $\mu$g/ml in plasma; more effectively inactivates Sindbis virus, by 6-fold, at a concentration of 300 $\mu$g/ml. Moreover, FIG. 14 shows that the former concentration of CARBOSTYRIL 124 with N-acetyl-L-cysteine is more effective than Photosensitizer A and N-acetyl-L-cysteine.

Inactivation by CARBOSTYRIL 124 and UVA of Bacteriophage $T_4$ is demonstrated in Example 6. Phage $T_4$ is a model for Parvo virus and Hepatitis A found in blood sample. The DNA of this virus is surrounded by capsid proteins which do not allow any sensitizer to get inside and kill the viral DNA. The goal is to inactivate the viral DNA without destroying the capsid proteins of the virus. There are blood clotting proteins, such as Factors VIII and IX, that are required throughout hemophiliacs' lives. Any sensitizer that would destroy the $T_4$ capsid proteins would also destroy the Factor VIII or Factor IX proteins. Thus, using Phage $T_4$ as a model for viruses found in the blood, it is intended to find a sensitizer that is able to destroy the $T_4$ virus without destroying the capsid proteins.

Note that none of the quinolone compounds tested to date have the carbon-halogen bond present in the preferred photosensitizers of the present invention.

The CARBOSTYRIL 124 compound is water soluble although it carries no formal charge. This is due to resonance structures that can form a zwitterionic species.

Figure 11A:
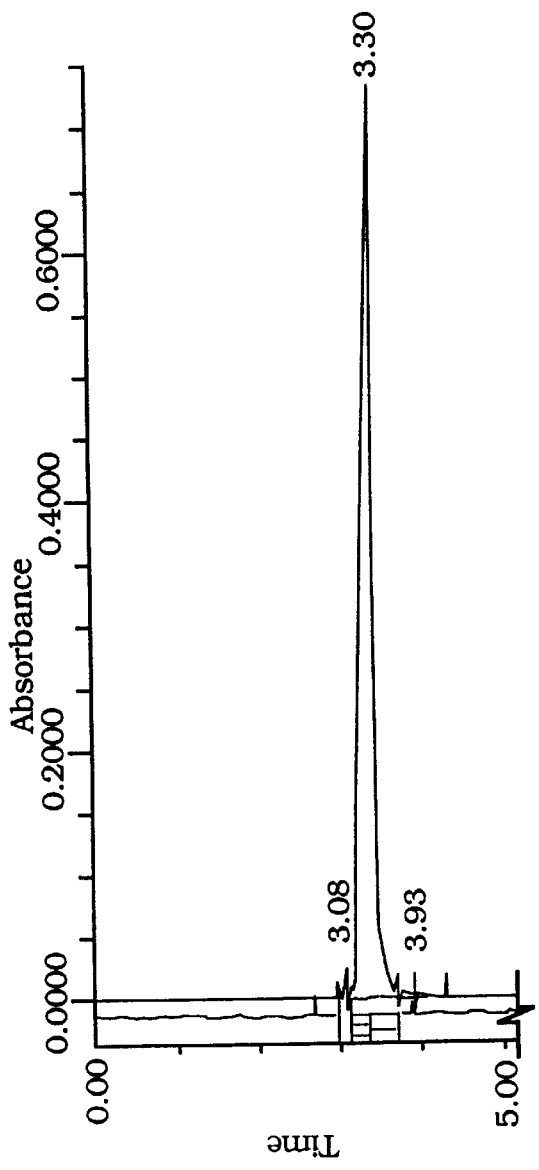
FIG. 11 shows HPLC chromatograms of a solution containing Photosensitizer QA before (FIG. 11A) and after 20 J/cm$^2$ UVA irradiation (FIG. 11B).
Figure 11B:
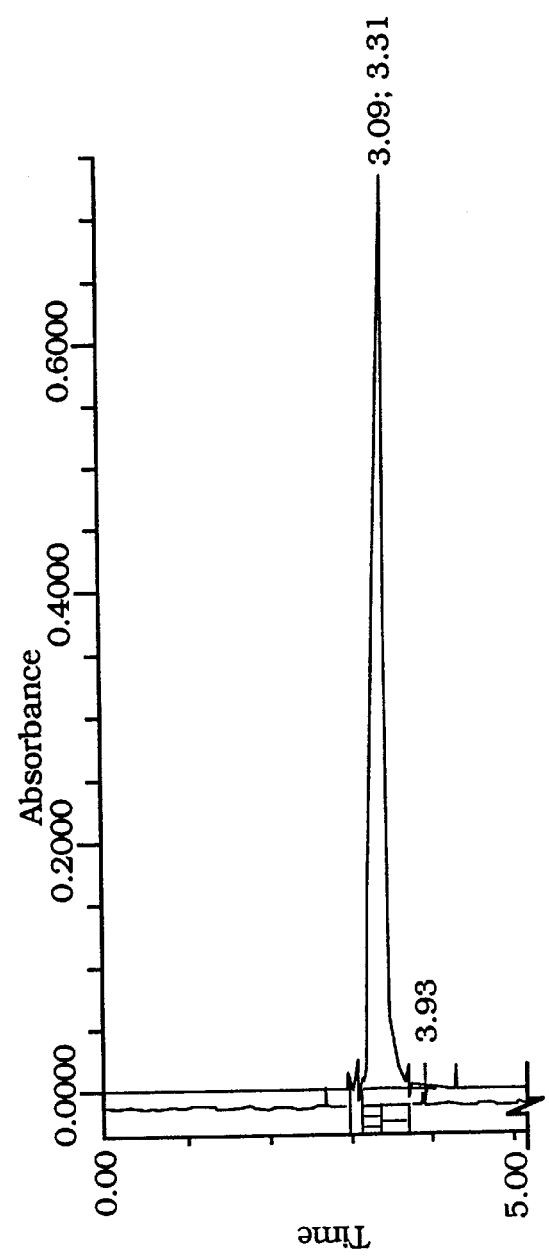

Three HPLC traces treated in saline with 0 J/cm$^2$ and 20 J/cm$^2$ of UVA light are shown in FIGS. 11A and B. No difference in the profiles can be seen following UVA irradiation, supporting the hypothesis that the nitrogen heterocyclic ring would be more resistant to photolysis. At 20 J/cm$^2$ of irradiation, over 99% of the total material is native Photosensitizer QA compound. Although the 3-bromoquinoline appears disappointing in its efficacy against Sindbis, this test needs to be repeated with excitation at a wavelength in the region of maximal absorbance of the compound (cal. 280–320 nm).

From the foregoing description, it will be realized that the invention can be used to selectively bind a chemical photosensitizer to blood-transmitted viruses, bacteria, or parasites. Also monoclonal or polyclonal antibodies directed against specific viral antigens (either coat proteins or envelope proteins) may be covalently coupled with a photosensitizer compound.

Since cell compositions also comprise a variety of proteins, the method of decontamination of cells described herein is also applicable to protein fractions, particularly blood plasma protein fractions, including, but not limited to, fractions containing clotting factors (such as Factor VIII and Factor IX), serum albumin and/or immune globulins. The viral and bacterial inactivation may be accomplished by treating a protein fraction with a photosensitizer as described herein.

Although described in connection with viruses, it will be understood that the methods of the present invention are generally also useful to inactivate any biological contaminant found in stored blood or blood products, including bacteria and blood-transmitted parasites.

The halogenated psoralens and coumarins according to the present invention are improved and more efficient photosensitizers because they require only a single UVA photon for activation. The ability of the halogen photosensitizer to react with any base pair imposes no limitation for the site of intercalation. Absorption of a UVA photon by a bromocoumarin in the presence of guanine (or any nucleotide base) leads to electron transfer and the formation of bound radicals and ultimately nucleic acid cleavage and viral or cell death. This cleavage mechanism is more efficient than the conventional crosslinking reaction of non-halogenated psoralens.

The coumarin radical can inflict damage on the nucleic acid double helix to which it is bonded by abstraction of a ribose (RNA) or deoxyribose (DNA) sugar carbon hydrogen bond. This can lead to DNA cleavage by known mechanisms. The guanine radical cation shown as an example is also known to react with molecular oxygen, initiating a series of reactions which cleave DNA. The byproduct of the bound radical photochemistry is debrominated coumarin, which is incapable of forming crosslinks to DNA unlike psoralens.

A preferred class of photosensitizers comprise nucleic acid intercalators which may be added to plasma or plasma fractions followed by UV irradiation to reduce the viral contamination therein. According to the present invention, the reduction of viral contamination can be unexpectedly reduced by utilizing halogenated intercalators. For example, it was observed that the bromopsoralens are about 200,000 times more effective in reducing viral activity when compared to use of their non-brominated counterparts.

The brominated intercalators are an improvement over the known psoralens and other substituted psoralens when used as photosensitizers because only one photon of light is required to activate the brominated photosensitizer whereas two photons are required to activate a non-brominated photosensitizer. Secondly, a brominated intercalator is effective in virtually every intercalative site, whereas a non-brominated photosensitizer is effective only in intercalation sites containing a uracil or thymine on different strands of the DNA or RNA. The brominated intercalators are also an improvement over the known coumarins, which unlike the known psoralens have no crosslinking ability and therefore have generally not been used previously as photosensitizers for viral inactivation, or as light activated drugs in therapeutic photophoresis procedures for certain cancer treatments and immune disorders.

The use of the brominated or halogenated intercalators is particularly useful for activation in hydrated systems such as plasma, immune sera, tissue culture media containing animal serum or serum components (such as fetal calf serum), or recombinant products isolated from tissue culture media.

The present invention may be applied to treatment of liquid blood in ex vivo irradiation, such as by methods and apparatus described in U.S. Pat. Nos. 4,889,129 and 4,878,891 and 4,613,322.

The photosensitizers also may be utilized in vivo and delivered in liposomes (artificial cells) or drug-loaded natural cells. After introduction of the liposome or drug-loaded cell, the patient may be treated by radiation to activate the photosensitizer.

The present invention is applicable to contaminants which comprise single or double-stranded nucleic acid chains, including RNA and DNA, and viruses, bacteria or other parasites comprising RNA and/or DNA.

The present invention includes the use of a "blocking" agent along with the photosensitizer in the method of inactivating contaminants in biological solutions. Such blocking agents prevent the photosensitizer from undergoing non-productive side reactions and side reactions that can lead to a reduction in the physiological properties of the components of the biological solution. The blocking agents of the present invention act predominantly by preventing reactions of the photosensitizer that lead to the formation of reactive byproducts that are not associated with reactive oxygen species such as singlet oxygen.

Three advantages were observed when selected "blocking" agents are used with either Photosensitizer A or Photosensitizer B: 1) improved cell quality as measured by functional assays, 2) retention of viral inactivation effectiveness, and 3) a dramatic suppression in the formation of ring-opened photolysis products after exposure of either Photosensitizer A or Photosensitizer B to UVA light.

1. Improved Cell Quality.

Figure 3:
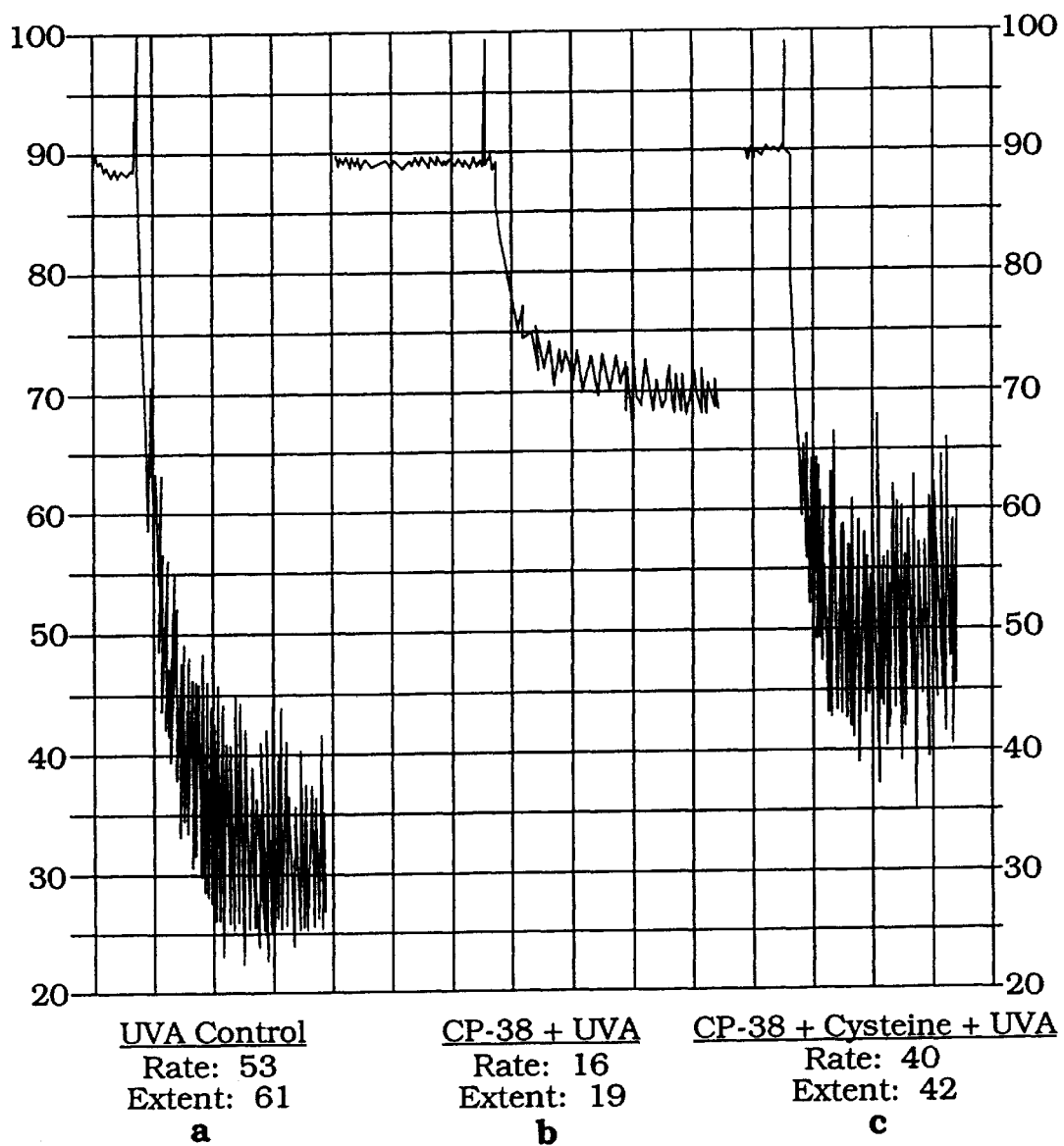
FIG. 3 depicts the aggregation response to ristocetin of control (a), Photosensitizer B (b), and Photosensitizer B and blocking agent cysteine (c).
Figure 4:
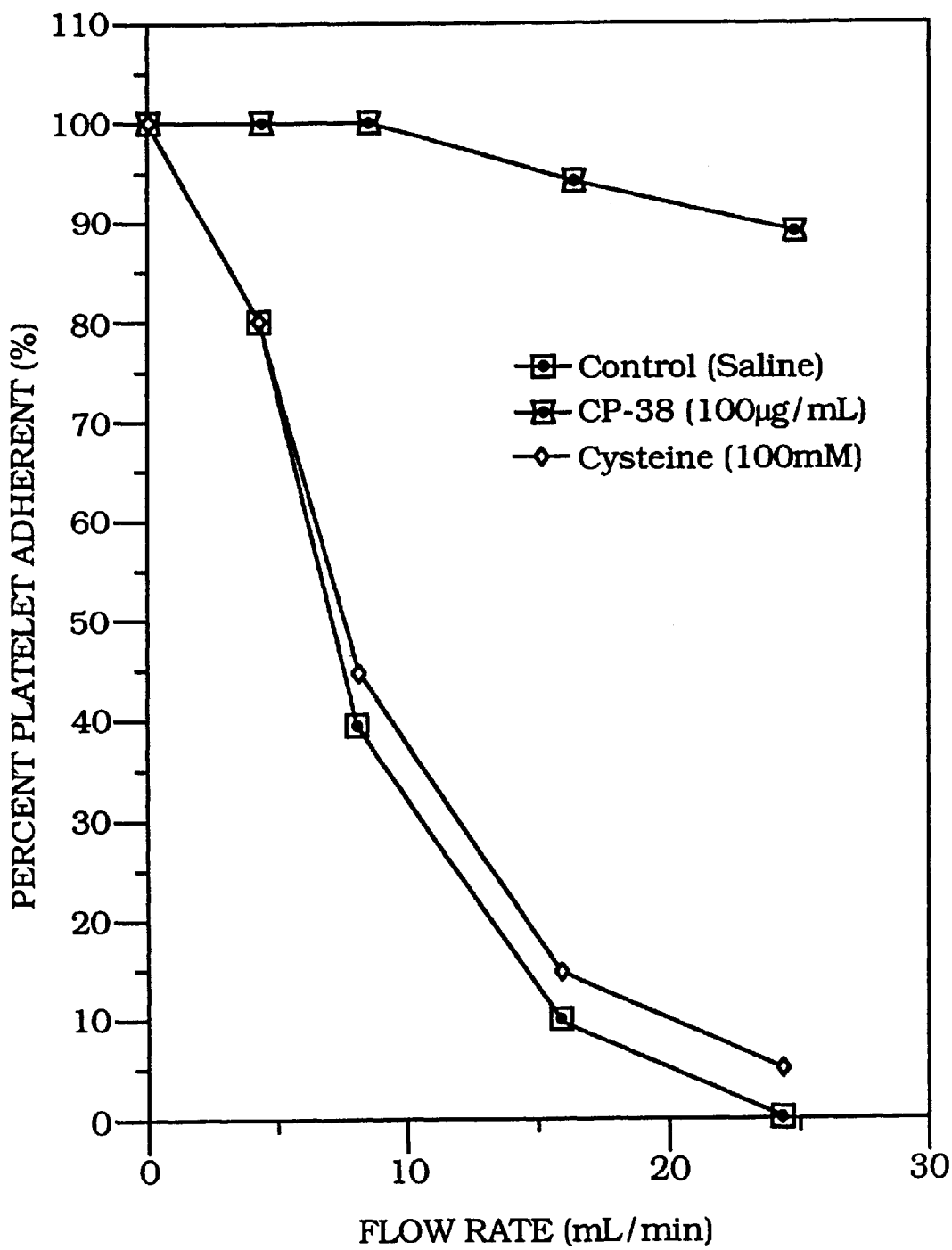
FIG. 4 is a plot showing the adhesion of platelets to protein coated glass slides following irradiation. The graph plots percentage platelet adherent versus flow rate for control (-□-), Photosensitizer B (-■-), and cysteine (-◇-).

Examples 1, 2 and 3 and FIGS. 3 and 4 demonstrate that use of cysteine blocking agents improves the functional quality of treated platelets, as measured by three in vitro assays: IgG binding, aggregation induced by Ristocetin, and cell adhesion to an artificial substrate. A brief description of each assay is provided. The IgG binding assay is most important, since any alterations to the cell surface chemistry that induce nonspecific binding of plasma IgG cause rapid in vivo removal of the circulating blood cells by the immune system.

Figure 2:
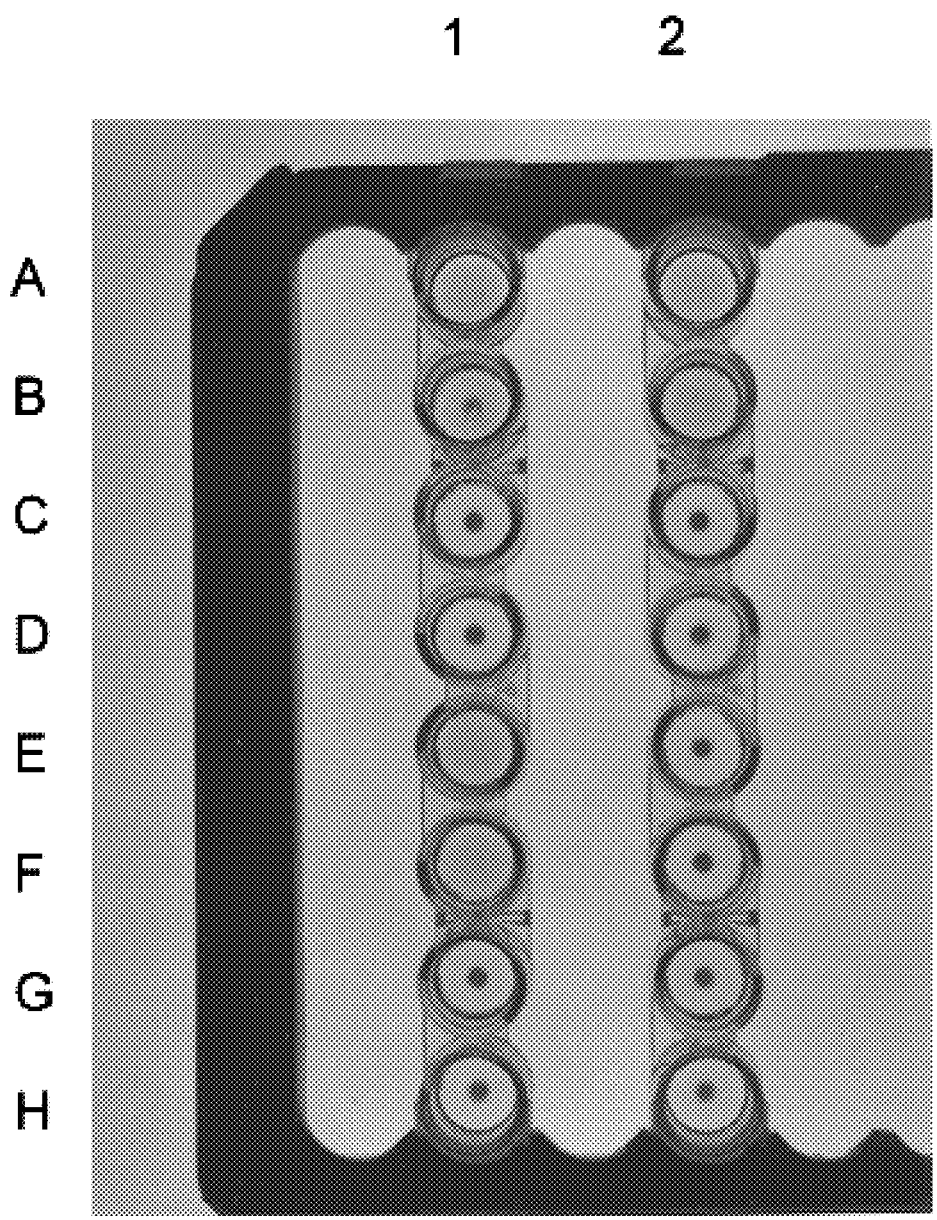
FIG. 2 shows the results of Capture-P assay for Photosensitizers A and B in the presence and absence of blocking agent cysteine.

Table 1 summarizes the IgG binding data, using numerous agents in combination with Photosensitizer A and UVA radiation with human platelets. The assay used was in a commercial test kit sold by Immucor Inc. for detection of IgG binding to platelets ("Capture-P Assay"). A photograph of one such developed assay is included in FIG. 2. As shown in Table 1, some classical antioxidants such as ascorbate are effective in blocking IgG binding to the cells, but other quenchers such as mannitol and glucose are ineffective. Degassing is also effective, as are certain reducing agents (DTT) and food preservatives (BHT, BHA), which act as antioxidants. However, certain amino acids such as cysteine, tyrosine, histidine and tryptophan are also effective, and these do not fit the antioxidant mold. The data in Table 1 demonstrate that oxidative reactions play a causative role, however, it also appears that other chemical reactions are involved. Therefore, selection of a useful "blocking" agent is a complex process.

The conclusions in Table 2 show that cysteine and ascorbate work best to suppress IgG binding to platelets post-irradiation using Photosensitizer B. Of these candidate species, the related N-acetyl-L-cysteine is the preferred compound of the invention, since it is as effective as cysteine or ascorbate in preventing IgG binding, but in addition is commercially available in pharmaceutical grade, and exhibits better storage properties in solution with halogenated sensitizers.

FIGS. 3 and 4 show the aggregation response data and the adhesion assay data, respectively. Irradiation of platelets in the presence of cysteine and Photosensitizer B results in an aggregation response profile that is closer to normal than irradiation with Photosensitizer B alone. Similarly, in FIG. 4 the ability of platelets subjected to a flow rate over a protein-coated surface to attach (indicative of their aggregation activation state) is minimized using cysteine, and greatly induced by Photosensitizer B+UVA alone (i.e., the cysteine treated platelets flow normally as they would in circulation, and do not behave like activated cells).

2. Effective Virus Kill in the Presence of N-acetyl-L-Cysteine.

Figure 5:
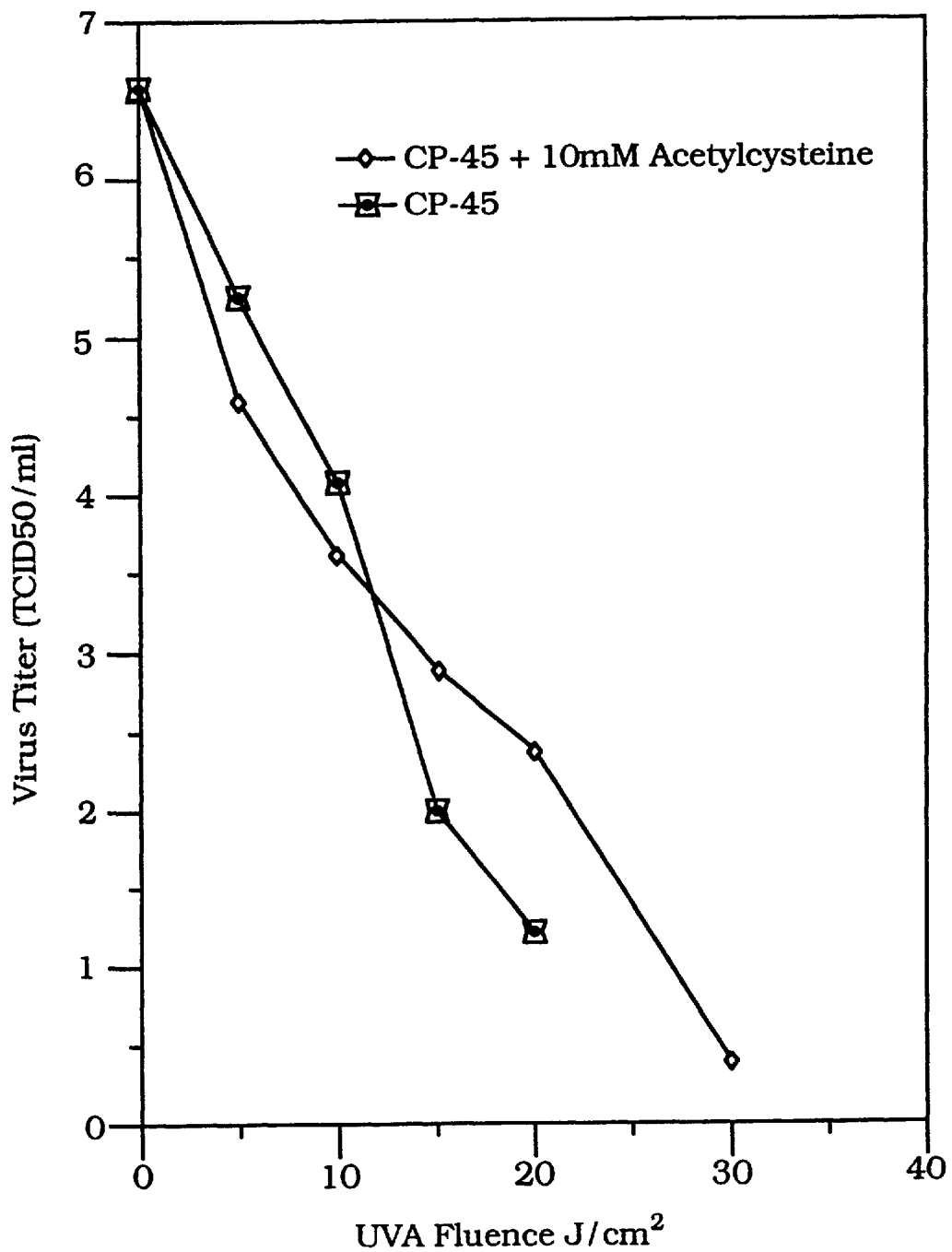
FIG. 5 is a plot showing the kinetics of inactivation of Sindbis virus using 218 $\mu$M Photosensitizer A with (-◆-) and without (-■-) 10 mM N-acetyl-L-cysteine in human plasma. The graph plots virus titer versus UVA fluence.
Figure 6:
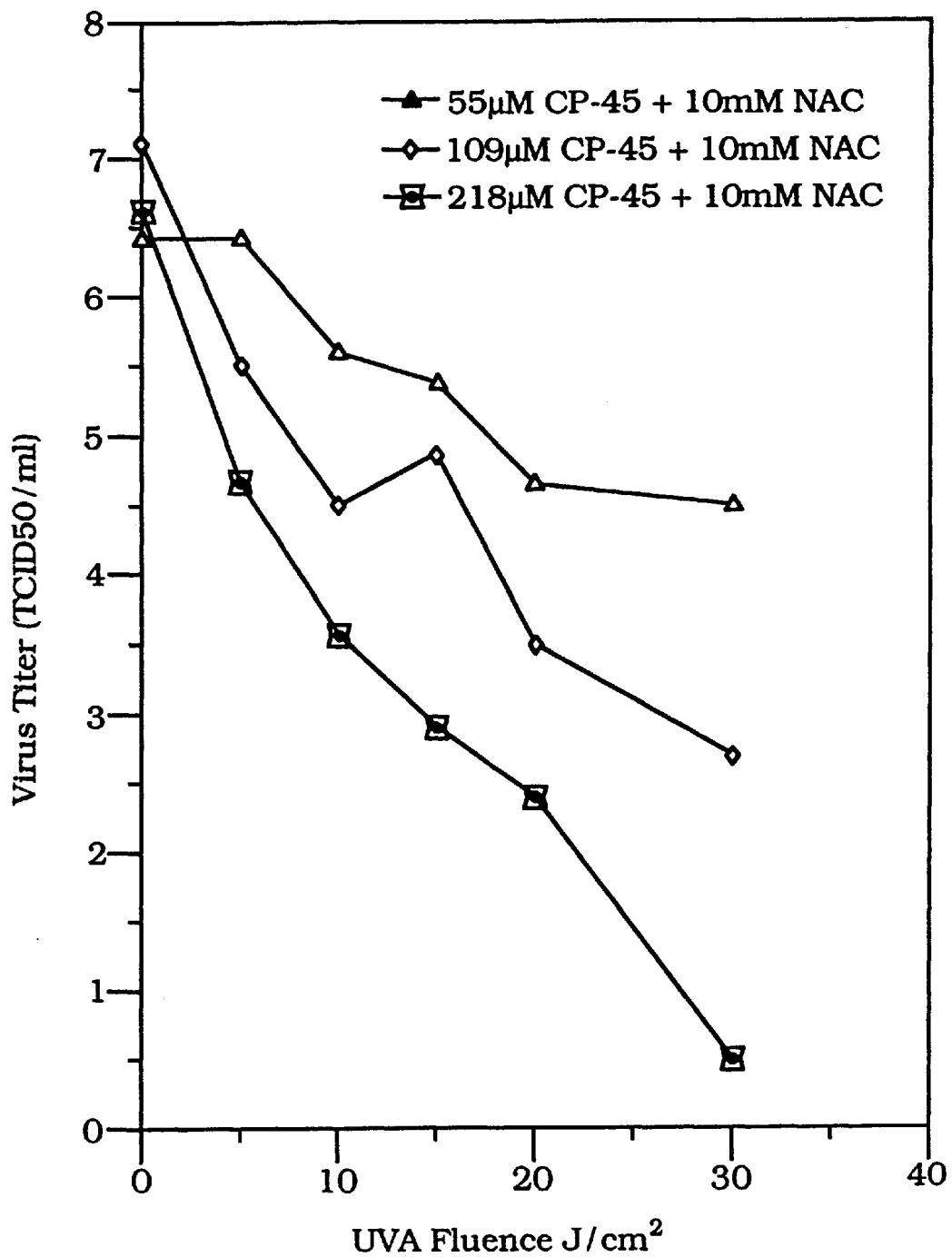
FIG. 6 is a plot showing the inactivation of Sindbis virus using 55 $\mu$M (-▲-), 109 $\mu$M (-◆-) and 218 $\mu$M (-■-) of Photosensitizer A with 10 mM N-acetyl-L-cysteine in plasma. The graph plots virus titer versus UVA fluence.
Figure 7:
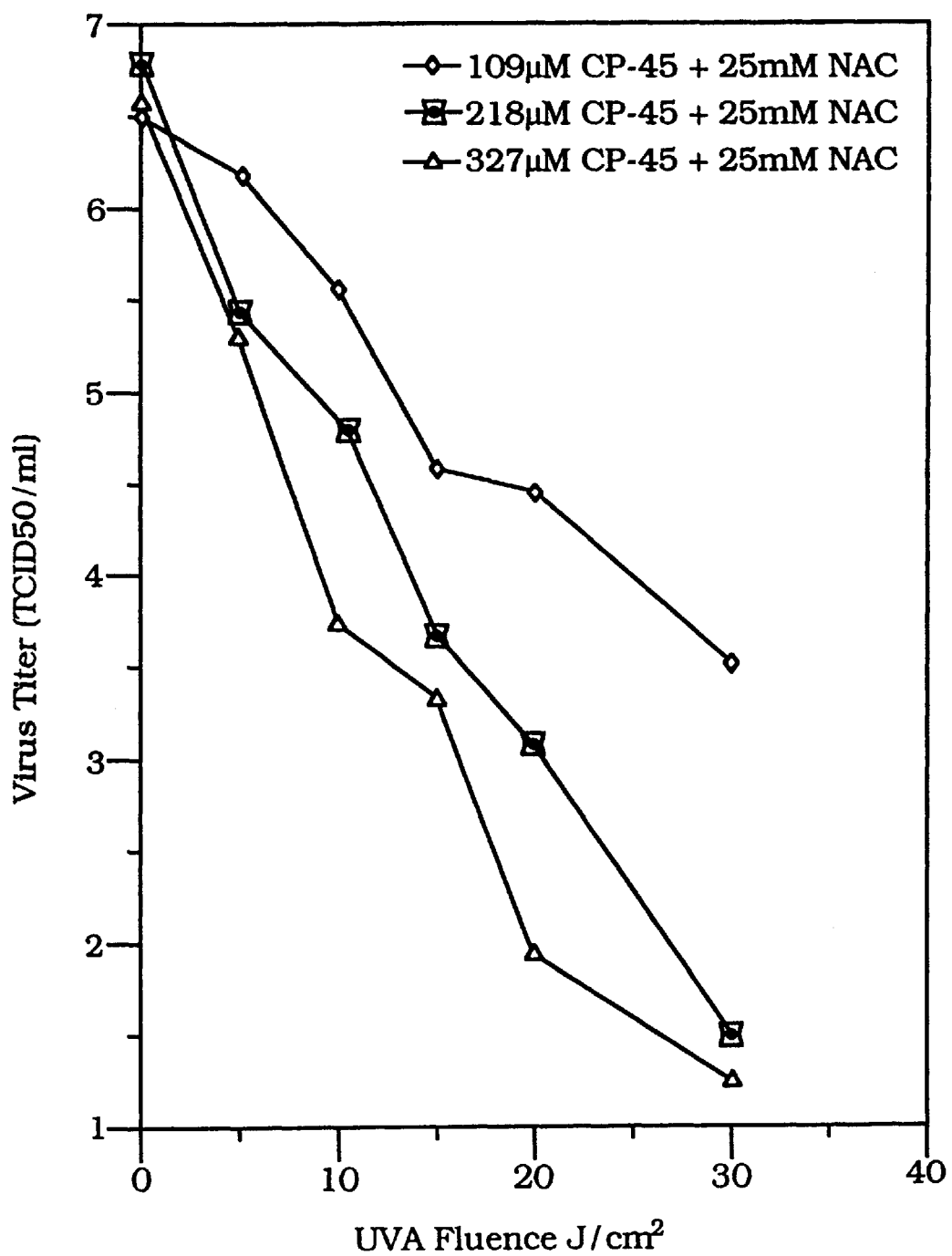
FIG. 7 is a plot showing the inactivation of Sindbis virus using 109 $\mu$M (-◆-), 218 $\mu$M (-■-) and 327 $\mu$M (-▲-) of Photosensitizer A with 25 mM N-acetyl-L-cysteine in plasma. The graph plots virus title versus UVA fluence.

The data shows that N-acetyl-L-cysteine does not inhibit the viral inactivation efficacy of Photosensitizer A+UVA light. FIG. 5 shows a comparison between Photosensitizer A alone and Photosensitizer A+10 mM N-acetyl-L-cysteine for inactivation of Sindbis virus, a mammalian enveloped RNA virus. FIG. 6 shows the dose dependence of viral kill with increasing concentrations of Photosensitizer A in the presence of 10 mM N-acetyl-L-cysteine. FIG. 7 shows a similar experiment using 25 mM N-acetyl-L-cysteine. In all cases the inclusion of the "blocking" agent did not affect the viral inactivation kinetics or dose dependence.

3. Presence of N-acetyl-L-Cysteine Inhibits Formation of Undesired Photosensitizer A Photolysis Products.

FIG. 8 shows two HPLC traces of Photosensitizer A exposed to UVA light in saline solution. Trace 1 shows the profile of Photosensitizer A irradiated by itself. Residual amounts of Photosensitizer A parent compound are seen as peak 4.36 (some 0.72% of the total material). The main peak at 3.53 corresponds to the debrominated Photosensitizer A, accounting for some 61% of the material. The remaining peaks, accounting for some 38% of the total material comprises various photolysis products of Photosensitizer A, which are believed to include a mixture of the possible ring-opened structures shown in FIG. 1 (each ring-opened product can exist in a brominated or debrominated form). These HPLC data clearly show that one mechanism of action of the "blocking" agent may be to block formation of reactive ring-opened compounds, which can in turn react with cells via their aldehyde or carboxylic acid groups. In addition, similar profiles are seen with Photosensitizer B, only more photolysis products are evident in the absence of a blocking agent since the psoralen nucleus can open at either the furan or pyrone rings.

EXAMPLE 1

IMMUNOGLOBULIN BINDING ASSAY

Immunoglobulin (IgG)-sensitized platelets are phagocytosed by the monocytes and macrophages of the reticuloendothelial system (RE). RE cells are located throughout the body but are concentrated in the spleen, liver, lungs and bone marrow. Platelets can be immune sensitized by several ways, e.g. platelet specific antigens, etc. Platelets can be IgG-sensitized by nonspecific binding of IgG to platelets which contributes to accelerated immune clearance. IgG binding to platelets can be easily detected by using the Immucor Capture-P assay (Capture-P, solid phase system for the detection of antibodies to platelets, Immucor Inc. Norcross, Ga. 30071.

Platelet concentrates or platelet rich plasma were irradiated to deliver 10 to 30 J/cm$^2$ in the presence of sensitizers Photosensitizer B and Photosensitizer A (100 µg/mL or 300 µg/mL) and blocking agents under investigation (10 or 20 mM, see Tables 1 and 2). Following photoinactivation treatment the platelets were analyzed by the Capture-P assay. The results are summarized in Table 1 (Photosensitizer B) and Table 2 (Photosensitizer A). Test results are interpreted as positive (+) for IgG binding (IgG sensitized) and negative (−) for non-binding (absence of IgG sensitization) according to the text kit manufacturer's described method.

EXAMPLE 2

RISTOCETIN AGGREGATION RESPONSE

Aggregation of platelets to form plugs at sites of hemorrhage is a pivotal reaction in the hemostatic response. This phenomenon is dependent upon the changes in the surface properties of circulating platelets which permits them to adhere to one another. Interaction of platelets with coagulation factors is involved in the aggregation phenomenon. In vitro binding of plasma von Willebrand factor to platelets, and platelet aggregation can be triggered by addition of Ristocetin as an agonist.

Photoinactivation treatment in the presence of sensitizer Photosensitizer B reduces the aggregation response of platelets to Ristocetin agonist compared to control (FIG. 3). However, the presence of cysteine (FIG. 4) and the other agents listed in table 1 during the photoinactivation treatment reduces the platelet aggregation damage. Aggregation response was measured in an aggregometer using 2.5 mg/mL final concentration.

EXAMPLE 3

ADHESION ASSAY

The adhesion property of photoinactivated platelets was measured using a micro flow system equipped with syringe pump and a microscope. Photoinactivated platelets were allowed to rest on glass flow cells in the presence of plasma. Following incubation at 37° C. for 30 minutes different shear stress was applied by pumping plasma with different flow rates. Adherent cells were quantitated and compared with controls. The results are shown in FIG. 4. These results clearly demonstrate that the presence of cysteine during photoinactivation substantially reduces adhesive properties of platelets (stickiness) compared to the sample without cysteine.

EXAMPLE 4

EFFECT OF DIFFERENT CONCENTRATIONS OF PHOTOSENSITIZER A AND N-ACETYL-L-CYSTEINE IN VIRUS INACTIVATION

Aliquots of a known titer of Sindbis virus ≧6 logs were spiked into STERICON bags. Two sets of three bags each were used. The first set contained 109, 218 and 327 µM Photosensitizer A and 25 mM N-acetyl-L-cysteine (NAC) and the second set contained 55, 109 and 218 µM Photosensitizer A and 10 mM NAC. Two other bags served as controls, each containing saline instead of the sensitizer. The bags were exposed to different levels of ultraviolet light A, except for the controls that were exposed to normal light. Samples were taken at 0, 5, 10, 15, 20 and 30 J/cm$^2$ and assayed for the presence of virus using VERO cells by the 50% tissue culture infectious dose (TCID50) endpoint titration.

The results of this experiment indicate that virus inactivation is sensitizer and NAC concentration dependent (FIGS. 5 and 6 and 7). The viral inactivation capacity of 100

μg/mL of Photosensitizer A and 10 mM N-acetyl-L-cysteine was ≧6 logs of Sindbis compared to 5 logs with 100 μg/mL and 25 mM N-acetyl-L-cysteine. These results also show that 50 μg/mL of Photosensitizer A achieved significant viral inactivation of 3 and 4 logs of virus with 25 mM and 10 mM N-acetyl-L-cysteine, respectively.

EXAMPLE 5

EVALUATION OF SINDBIS VIRAL INACTIVATION CAPACITY OF SEVERAL QUINOLONES

The Sindbis viral inactivation capacity of several quinolones including Photosensitizer QA, Photosensitizer QB and CARBOSTYRIL 124 was tested (FIG. 9). Aliquots of a known titer of Sindbis virus ≧6 logs were spiked into Stericon bags. Each bag contained 300 μg/mL of Photosensitizer QA, Photosensitizer QB and CARBOSTYRIL 124, respectively. One bag containing saline instead of the sensitizer served as a control. The bags were exposed to different levels of ultraviolet light A, except for the controls that were exposed to normal light. Samples were taken at 0, 5, 10, 15, 20 and 30 J/cm$^2$ and assayed for the presence of virus using VERO cells by the 50% tissue culture infectious dose (TCID50) endpoint titration.

The results from this study show that all the three quinolones have viral inactivation capacity (FIG. 9). However, CARBOSTYRIL 124 was the best with ≧6 logs of virus reduction. Photosensitizer QA and Photosensitizer QB killed 2 and 4 logs of Sindbis respectively. Viral inactivation with Photosensitizer QB and Photosensitizer QA was done without N-acetyl-L-cysteine; however, virus inactivation with CARBOSTYRIL 124 was done with and without N-acetyl-L-cysteine (FIG. 10). N-acetyl-L-cysteine did not interfere with the viral inactivation capacity of CARBOSTYRIL 124.

EXAMPLE 6

INACTIVATION OF A NONENVELOPED VIRUS BY CARBOSTYRIL 124 (7-AMINO,4-METHYL, 2-HYDROXY QUINOLINE) AND ULTRAVIOLET LIGHT

Bacteriophage $T_4$, a nonenveloped bacterial virus, was used to examine inactivation by CARBOSTYRIL 124 and ultraviolet light. $T_4$ is known to be quite resistant to inactivation and has been shown to be resistant to both CP-38 and CP-45 (data not shown).

A lyophilized *E. coli* bacterial pellet was obtained from ATCC. Said pellet was suspended in 1.0 mL of LB medium by vortexing. A portion of the bacterial suspension was picked up with a sterilized inoculating loop and streaked on the lawn of an LB plate. The streaked plate was placed in an incubator for 24 hours at 37° C. in order to grow isolated bacterial colonies. A colony of bacteria was picked up with the sterile platinum loop and washed with 50 mL of LB medium and 0.5 mL of 20% maltose solution in a screw cap flask. The flask was then left on a roller drum at 120 rpm in an incubator at 37° C., with a loosened flask cap to ensure proper aeration to yield a saturated bacterial suspension. Next, the suspension was transferred into a sterile tube and centrifuged at 5000 rpm for 10 minutes, the supernatant subsequently discarded. The resulting bacterial pellet was resuspended in about 50 mL of 0.1 M magnesium sulfate solution and stored in a refrigerator.

The lyophilized $T_4$ pellet obtained form ATCC was reconstituted with 0.3 mL of LB medium by vortexing in a small sterile vial. 100 μL of the resulting viral solution was removed for a 10-fold serial dilution.

To effect the serial dilution, 900 μL of SM medium were introduced into 6 sterile culture tubes. 100 μL of viral suspension was transferred from the original viral solution into the first culture tube. The tube was then vortexed and 100 μL of suspension from the first culture tube was transferred to the second culture tube. This process being repeated until the six serial dilutions into the six culture tubes were achieved.

Next, 100 μL of each of the six prepared viral dilutions were placed into a second set of six sterile culture tubes. To each of the six culture tubes, 100 μL of previously prepared bacterial suspension was added. The six tubes were then incubated at 37° C. for about 30 minutes to allow the $T_4$ virus to infect the *E. coli* bacteria.

After infection, 2.8 mL of molten LB top agar was introduced into each of the culture tubes, gently vortexed and poured over a lawn of previously prepared and labeled LB plates. After hardening, the plates were placed in an incubator at 37° C. overnight.

The viral titer was obtained by the plaque forming assay. By counting plaque number on countable plates, the viral titer was determined to be:

Viral Titer=(# of plaques)×10(# of dilution+1)

The viral stock solution for the viral inactivation experiment was prepared by isolating the plates of a very large number of clear plaques. To each of them was added 3 mL of SM medium. The plates were then left in the refrigerator for 7 hours. Next, the plates were scraped off and the supernatant was placed in a centrifuge tube and centrifuged at 5000 rpm for 15 minutes. The viral supernatant was then separated and stored with a drop of distilled chloroform at 4° C.

The effect of the sensitizer CARBOSTYRIL 124 (7-amino,4-methyl,2-hydroxy quinoline) on the $T_4$ virus was studied by the plaque assay method. $T_4$ virus was exposed to 100 μg/mL of sensitizer for 24 hours, after which it was exposed to UV light for 10 minutes, estimated to be 3–4 J/cm$^2$. The effects on the viral titer after exposure are shown in Table 4.

The experimental data show that starting with a virus titer of 1.5×10$^9$ plaque-forming units (pfu) and adding CARBOSTYRIL 124 dissolved in either phosphate-buffered saline (PBS) or 7% bovine serum albumin in PBS, resulted in residual virus titers of 2.0×10$^6$ pfu or 1.0×10$^5$ pfu, respectively. Approximately a 3 log$_{10}$ reduction is shown by these data using a PBS suspension of sensitizer, which is marginally soluble in PBS. A 4 log reduction is shown in the BSA/PBS suspension, which helped the solubility of the sensitizer somewhat. A low does of UVA light, estimated at about 3–4 J/cm$^2$, was used in all cases. Although the sensitizer concentration was theoretically 100 μg/mL, due to the solubility problem the actual concentration in solution was probably less.

The above data show significant inactivation (3–4 log) of a nonenveloped model virus that has been shown resistant to may treatments. Moreover, these data serve as a model for human pathogens such as hepatitis A and parvo virus B19. Inactivation was achieved using low concentrations of a marginally water soluble molecule, at low UVA doses, supporting the use of quinolines and/or quinolones as photosensitizers for viral inactivation. Further, the viral inactivation characteristics of CARBOSTYRIL 124 can be enhanced by the addition of halogen and charged sidechain features.

TABLE 1

Summary of Capture-P Results
Sensitizer CP-38

| Compound | Conc. (mM) | Capture-P Test (-/+) |
|---|---|---|
| Deoxygenation | — | - |
| L-Histidine | 25 | - |
| L-Cysteine | 10 | - |
| L-Tyrosine | 25 | - |
| L-Tryptophan | 25 | - |
| Ascorbate | 10 | - |
| N-Acetyl Cysteine | 25 | - |
| Propyl gallate | 25 | - |
| Glutathione | 25 | - |
| Mercaptopropionylgylcine | 10 | - |
| Dithiothreotol (DTT) | 5 | - |
| BHT | 25 | - |
| BHA | 25 | - |
| L-Lysine | 10 | + |
| L-Serine | 10 | + |
| L-Methionine | 10 | + |
| Glucose | 100 | + |
| Mannitol | 20 | + |
| Trolox | 5 | + |
| Serine + Methionine | 10 | + |
| Glycerol | 2% | + |

TABLE 2

Summary of Capture-P Results
Sensitizer CP-45

| Compound | Conc. (mM) | Capture-P Test (-/+) |
|---|---|---|
| L-Cysteine | 10 | - |
| Ascorbate | 10 | - |
| N-Acetyl Cysteine | 10 | - |

TABLE 3

FE: VI-85 Summary

Samples:
1. Pooled PRP in Stericon container
2. Pooled PRP + 100 µg/mL Carbostyril In 0.9% saline + 10 J/cm²UVA energy

TABLE 3-continued

FE: VI-85 Summary

3. Pooled PRP + 100 µg/mL Carbostyril in 0.9% saline + 30 J/cm²UVA energy
4. Pooled PRP + 300 µg/mL Carbostyril in 0.9% saline + 10 J/cm²UVA energy
5. Pooled PRP + 300 µg/mL Carbostyril in 0.9% saline + 30 J/cm²UVA energy Results:

| Assay | #1 (control) | #2 | #3 | #4 | #5 |
|---|---|---|---|---|---|
| Morphology (score) | 358 | 226 | 210 | 305 | 300 |
| HSR (%) | 75 | 38 | 24 | 32 | 55 |
| Aggregation Resp. to Collagen (%) | 68 | 22 | 0 | 0 | 0 |
| Aggregation Resp. to Ristocetin (%) | 65 | 26 | 24 | 28 | 12 |

TABLE 4

Effect on the vital titer after exposing it to 7-amino, 4-methyl, 2-hydroxy quinoline and 10 min of UV light:

| Description | Control (Pure Virus) | Case I | Case II |
|---|---|---|---|
| Plate # | 6 | 3 | 2 |
| Plaque # | 150 | 200 | 100 |
| Viral Titer (pfu) | $1.5 \times 10^9$ | $2.0 \times 10^6$ | $1.0 \times 10^5$ |

Case I: The sensitizer was suspended in PBS buffer. The sensitizer was partially soluble in the buffer while some of it remained as a suspension in the PBS buffer.
Case II: The sensitizer was suspended in 7% BSA solution on PBS buffer.
The structure of the 7-amino, 4-methyl, 2-hydroxy quinoline is:

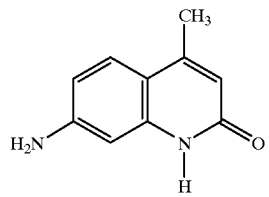

TABLE 5

Carbostyril Evaluation
6/2/95

| Sample Description | Cell Count (thsn/cu mm) | HSR (%) | Morphology Score | Aggregation (Ristocetin) Rate | Extent | Aggregation (Collagen) Rate | Extent | pH |
|---|---|---|---|---|---|---|---|---|
| Untreated | 985 | 78.84 | 341 | 68 | 72 | 19 | 25 | 7.53 |
| #1 16.7 ug/mL | 860 | 22.44 | 282 | 9 | 10 | 1 | 2 | 7.44 |
| #2 16.7 ug/mL + NAC | 935 | 20.85 | 221 | 70 | 75 | 2 | 4 | 6.59 |
| #3 *25 ug/mL | 835 | 23.92 | 291 | 3 | 5 | 0 | 0 | 7.38 |
| #4 *25 ug/mL + NAC | 875 | 19.05 | 209 | 59 | 65 | 1 | 4 | 6.59 |

NAC = 10 mM N-Acetyl Cysteine
*Approximate concentration due to limits of solubility. Amount of carbostyril compound measured = 150 ug/mL

What is claimed is:

1. A method of reducing the ring-opening of psoralen compounds having at least one halogen substituent or at least one non-hydrogen bonding ionic moiety or both or of coumarin compounds upon irradiation, said compounds being present in a mixture in which they are in contact with a virus or cell comprising the steps of:
   a) mixing said virus or cell mixture containing said psoralen or coumarin compound with a blocking agent selected from the group consisting of histidine, cysteine, tryrosine, tryptophan, ascorbate, N-acetyl cysteine, propyl gallate, mercaptopropionyl glycine, butylated hydroxytoluene (BHT) and butylated hydroxyanisole (BHA); and
   b) irradiating the resulting mixture whereby said ring-opening reaction is reduced.

2. The method of claim 1 wherein said blocking agent reduces opening of a furan or a pyrone ring.

3. The method of claim 1 wherein the blocking agent is an antioxidant.

4. The method of claim 1 wherein the coumarin compound has at least one halogen atom or at least one non-hydrogen bonding ionic moiety.

5. A method of reducing irradiation-induced photosensitizer damage to platelets and red blood cells in a biological mixture, comprising the steps of:
   a) mixing said biological mixture with the photosensitizer which is selected from the group consisting of nucleic acid intercalators having at least one halogen substituent or at least one non-hydrogen bonding ionic moiety or both, and coumarins; and a blocking agent selected from the group consisting of histidine, cysteine, tyrosine, tryptophan, ascorbate, N-acetyl cysteine, propyl gallate, mercaptopropionylglycine, butylated hydroxytoluene (BHT) and butylated hydroxyanisole (BHA); and
   b) irradiating the mixture whereby said blocking agent reduces photolysis of said photosensitizer thereby reducing irradiation-induced damage to the platelets or red blood cells.

6. The method of claim 5, wherein said coumarin compound has at least one halogen atom or at least one non-hydrogen bonding ionic moiety.

7. The method of claim 5 wherein said blocking agent reduces opening of a furan or pyrone ring of said photosensitizer.

8. The method of claim 5 wherein the blocking agent is an antioxidant.

9. The method of claim 5 wherein the blocking agent enhances the antiviral, anti-bacterial or anti-parasitic activity of said photosensitizer in said biological mixture.

10. The method of claim 5 wherein the biological mixture substantially retains its biological activity.

* * * * *